US011813480B2

(12) United States Patent
Liu

(10) Patent No.: US 11,813,480 B2
(45) Date of Patent: Nov. 14, 2023

(54) SYSTEMS AND METHODS FOR GENERATING A DOSE DISTRIBUTION

(71) Applicant: SHANGHAI UNITED IMAGING HEALTHCARE CO., LTD., Shanghai (CN)

(72) Inventor: Yanfang Liu, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 0 days.

(21) Appl. No.: 17/453,888

(22) Filed: Nov. 8, 2021

(65) Prior Publication Data
US 2022/0054859 A1    Feb. 24, 2022

Related U.S. Application Data

(63) Continuation of application No. 16/711,612, filed on Dec. 12, 2019, now Pat. No. 11,167,152.

(30) Foreign Application Priority Data

Dec. 12, 2018 (CN) .......................... 201811517635.3

(51) Int. Cl.
*A61N 5/10* (2006.01)
*G06N 20/00* (2019.01)
*A61N 5/06* (2006.01)

(52) U.S. Cl.
CPC ............ *A61N 5/1031* (2013.01); *G06N 20/00* (2019.01); *A61N 2005/0627* (2013.01); *A61N 2005/1034* (2013.01)

(58) Field of Classification Search
CPC .......... A61N 5/1031; A61N 2005/0627; A61N 2005/1034; G06N 20/00
See application file for complete search history.

(56) References Cited

U.S. PATENT DOCUMENTS

| 2005/0143965 | A1 | 6/2005 | Failla et al. |
| 2006/0145088 | A1* | 7/2006 | Ma .......................... H05H 15/00 |
| | | | 250/396 ML |

(Continued)

FOREIGN PATENT DOCUMENTS

| CN | 104407374 A | 3/2015 |
| CN | 205233527 U | 5/2016 |

(Continued)

OTHER PUBLICATIONS

First Office Action in Chinese Application No. 201811517635.3 dated May 27, 2020, 15 pages.

(Continued)

*Primary Examiner* — Hugh Maupin
(74) *Attorney, Agent, or Firm* — METIS IP LLC

(57) ABSTRACT

A system for generating a dose distribution is provided. The system may obtain a first dose distribution in at least a portion of a subject. The system may also obtain a trained machine learning model. The system may further generate, based on the first dose distribution and the trained machine learning model, a second dose distribution in the at least a portion of the subject, wherein the second dose distribution has a higher accuracy than that of the first dose distribution.

20 Claims, 8 Drawing Sheets

(56) References Cited

U.S. PATENT DOCUMENTS

| | | | | |
|---|---|---|---|---|
| 2015/0352374 | A1* | 12/2015 | Gattikker | A61N 5/1031 |
| | | | | 703/2 |
| 2016/0129282 | A1* | 5/2016 | Yin | A61N 5/1031 |
| | | | | 600/1 |
| 2017/0004267 | A1* | 1/2017 | Svatos | G16H 20/40 |
| 2017/0177812 | A1* | 6/2017 | Sjölund | G16H 20/40 |
| 2017/0304651 | A1 | 10/2017 | Takayanagi et al. | |
| 2018/0063386 | A1 | 3/2018 | Sharma et al. | |
| 2019/0192880 | A1 | 6/2019 | Hibbard | |
| 2019/0325620 | A1 | 10/2019 | Adler et al. | |
| 2020/0043573 | A1 | 2/2020 | Fält et al. | |
| 2021/0035340 | A1 | 2/2021 | Wang et al. | |

FOREIGN PATENT DOCUMENTS

| | | |
|---|---|---|
| CN | 107715314 A | 2/2018 |
| CN | 107875525 A | 4/2018 |

OTHER PUBLICATIONS

The Second Office Action in Chinese Application No. 201811517635.3 dated Dec. 28, 2020, 15 pages.

Lin, Guifen et al., De-Noising of Monte Carlo Dose Distribution Based on Three-Dimensional Savitzky-Golay Filter, Journal of Data Acquisition & Processing, 21(4): 439-443, 2006.

* cited by examiner

SYSTEMS AND METHODS FOR GENERATING A DOSE DISTRIBUTION

CROSS-REFERENCE TO RELATED APPLICATIONS

This application is a Continuation of U.S. application Ser. No. 16/711,612 filed on Dec. 12, 2019, which claims priority to Chinese Patent Application No. 201811517635.3, filed on Dec. 12, 2018, the contents of each of which are hereby incorporated by reference.

TECHNICAL FIELD

The disclosure generally relates to a radiotherapy field, and more particularly relates to systems and methods for dose distribution simulation.

BACKGROUND

Radiotherapy techniques are widely used for treating cancer. Before performing radiotherapy treatment, it is often necessary to calculate a radiation dose distribution in the body to ensure that a tumor area receives a therapeutic radiation dose, and that the radiation dose that a normal tissue receives is within a safe range. In general, a radiation dose distribution may be determined using a pencil beam algorithm, a cone convolution algorithm, a Monte Carlo algorithm, etc. However, the pencil beam algorithm and the convolution algorithm may quickly compute the radiation dose distribution, but with poor accuracy. The Monte Carlo algorithm provides higher accuracy, but with a lower computation speed. Thus, it is desired to provide systems and methods for generating a radiation dose distribution accurately and efficiently.

SUMMARY

According to a first aspect of the present disclosure, a system is provided. The system may include at least one storage device storing executable instructions, and at least one processor in communication with the at least one storage device. When executing the executable instructions, the at least one processor may cause the system to perform one or more of the following operations. The system may obtain a first dose distribution in at least a portion of a subject. The system may also obtain a trained machine learning model. The system may further generate, based on the first dose distribution and the trained machine learning model, a second dose distribution in the at least a portion of the subject, wherein the second dose distribution has a higher accuracy than that of the first dose distribution.

In some embodiments, the first dose distribution may describe a distribution of a first count of radiation particles in the at least a portion of the subject, and the first count may be less than a threshold.

In some embodiments, the second dose distribution may describe a distribution of a second count of radiation particles in the at least a portion of the subject, and the second count may exceed the first count.

In some embodiments, to obtain the first dose distribution in at least a portion of the subject, the at least one processor may cause the system to perform the operations including obtaining personalized data of the subject. The at least one processor may also cause the system to perform the operations including determining, based on the personalized data of the subject, the first dose distribution in the at least a portion of the subject using a Monte Carlo algorithm.

In some embodiments, the personalized data of the subject may include a radiotherapy treatment plan of the subject and a density distribution in the subject.

In some embodiments, the density distribution in the subject may be obtained based on image data of the subject.

In some embodiments, the radiotherapy treatment plan of the subject may include at least one of a value of an energy of a particle source, a penetration depth of radiation particles in the subject, an angle of a gantry of a radiation device, a shape of a radiation field collimated by a collimator, a radiation dose of the radiation device.

In some embodiments, to determine, based on the personalized data of the subject, the first dose distribution in the at least a portion of the subject using a Monte Carlo algorithm, the at least one processor may cause the system to perform the operations including obtaining a particle transport model. The at least one processor may also cause the system to perform the operations including generating, based on data of initial radiation particles and the radiotherapy treatment plan of the subject, radiation particles. The at least one processor may further cause the system to perform the operations including simulating, based on the density distribution in the subject, transport of each of the radiation particles in the particle transport model. The at least one processor may further cause the system to perform the operations including determining, based on the transport of each of the at least a portion of the radiation particles, the first dose distribution.

In some embodiments, the trained machine learning model may be obtained according to a process including obtaining a plurality of training samples. The trained machine learning model may also be obtained according to a process including generating the trained machine learning model by iteratively updating, based on the plurality of training samples, parameter values of a machine learning model in an iterative process.

In some embodiments, for each iteration of the iterative process, the iterative process may include inputting at least one training sample of the plurality of training samples into the machine learning model. For each iteration of the iterative process, the iterative process may also include generating, based on the at least one training sample, an estimated output using the machine learning model. For each iteration of the iterative process, the iterative process may further include obtaining an assessment result by assessing a difference between the estimated output and a reference output corresponding to the at least one training sample. For each iteration of the iterative process, the iterative process may include determining whether a termination condition is satisfied. In some embodiments, based on a determination whether the termination condition is satisfied, the iterative process may include updating, based on the assessment result, at least some of the parameter values of the machine learning model in response to the determination that the termination condition is not satisfied. Based on a determination whether the termination condition is satisfied, the iterative process may include designating the machine learning model with the parameter values updated in a last iteration as the trained machine learning model in response to the determination that the termination condition is satisfied.

In some embodiments, the obtaining an assessment result by assessing a difference between the estimated output and a reference output may include determining a value of a cost function relating to the difference between the estimated output and the reference output. The termination condition may relate to a cost function or an iteration count of the iterative process.

In some embodiments, each of the plurality of training samples may include a third dose distribution and a fourth dose distribution of a specific object, wherein the fourth dose distribution serves as the reference output of the machine learning model in the iterative process, and the third dose distribution serves as an input of the machine learning model in the iterative process, the third dose distribution describing a distribution of a third count of radiation particles, the fourth dose distribution describing a distribution of a fourth count of radiation particles, the fourth count exceeding the third count.

In some embodiments, the fourth count may be equal to two times of the third count.

In some embodiments, at least one of the third dose distribution or the fourth dose distribution may be determined based on personalized data of the specific object using a simulation technique, the personalized data of the specific object including a radiotherapy treatment plan of the specific object and a density distribution in the specific object.

In some embodiments, each of the plurality of training samples may include a third dose distribution of a specific object and a deviation between the third dose distribution and a fourth dose distribution of the specific object, wherein the deviation between the third dose distribution and the fourth dose distribution serves as the reference output of the machine learning model in the iterative process, the third dose distribution serves as an input of the machine learning model in the iterative process, the third dose distribution describing a distribution of a third count of radiation particles, the fourth dose distribution describing a distribution of a fourth count of radiation particles, the fourth count exceeding the third count.

In some embodiments, to generate, based on the first dose distribution and the trained machine learning model, the second dose distribution in the at least a portion of the subject, the at least one processor may cause the system to perform the operations including inputting the first dose distribution into the trained machine learning model. The at least one processor may also cause the system to perform the operations including designating an output of the trained machine learning model as the second dose distribution.

In some embodiments, to generate, based on the first dose distribution and the trained machine learning model, the second dose distribution in the at least a portion of the subject, the at least one processor may cause the system to perform the operations including inputting the first dose distribution into the trained machine learning model. The at least one processor may also cause the system to perform the operations including generating a deviation between the first dose distribution and the second dose distribution using the trained machine learning model by processing the first dose distribution. The at least one processor may further cause the system to perform the operations including determining, based on the first dose distribution and the deviation between the first dose distribution and the second dose distribution, the second dose distribution.

In some embodiments, to generate, based on the first dose distribution and the trained machine learning model, the second dose distribution in the at least a portion of the subject, the at least one processor may cause the system to perform the operations including inputting the first dose distribution and the personalized data of the subject into the trained machine learning model. The at least one processor may also cause the system to perform the operations including determining, based on an output of the trained machine learning model, the second dose distribution.

In some embodiments, the trained machine learning model may be obtained according to a process including obtaining a plurality of first training samples associated with different objects. The process may also include generating a preliminary trained machine learning model by training a machine learning model using the plurality of first training samples. The process may further include generating, based on the personalized data of the subject, a plurality of second training samples associated with the subject, each of the plurality of second training samples including a third dose distribution and a fourth dose distribution in the subject simulated based on the personalized data of the subject. The process may further include training the trained machine learning model by training the preliminary trained machine learning model using the plurality of second training samples.

According to a second aspect of the present disclosure, a method is provided. The method may be implemented on at least one computing device, each of which may include at least one processor and a storage device. The method may include obtaining a first dose distribution in at least a portion of a subject. The method may also include obtaining a trained machine learning model. The method may further include generating, based on the first dose distribution and the trained machine learning model, a second dose distribution in the at least a portion of the subject, wherein the second dose distribution has a higher accuracy than that of the first dose distribution.

According to a third aspect of the present disclosure, a non-transitory computer-readable medium storing at least one set of instructions is provided. When executed by at least one processor, the at least one set of instructions may direct the at least one processor to perform a method. The method may include obtaining a first dose distribution in at least a portion of a subject. The method may also include obtaining a trained machine learning model. The method may further include generating, based on the first dose distribution and the trained machine learning model, a second dose distribution in the at least a portion of the subject, wherein the second dose distribution has a higher accuracy than that of the first dose distribution.

According to a fourth aspect of the present disclosure, a system is provided. The system may include at least one storage device storing executable instructions, and at least one processor in communication with the at least one storage device. When executing the executable instructions, the at least one processor may cause the system to perform one or more of the following operations. The system may include obtaining a plurality of training samples, each of the plurality of training samples includes a first dose distribution and a second dose distribution of a subject, or the first dose distribution and a difference between the first dose distribution and the second dose distribution. The system may also include generating a trained machine learning model by iteratively updating, based on the plurality of training samples, parameter values of a machine learning model in a training process, wherein the first dose distribution describes a distribution of a first count of radiation particles in the subject and the second dose distribution describes a distribution of a second count of radiation particles in the subject, the second count exceeding the first count.

In some embodiments, the iteratively updating, based on the plurality of training samples, parameter values of a machine learning model may include performing an iterative process. For each iteration of the iterative process, the iterative process may include inputting at least one training sample of the plurality of training samples into the machine learning model. For each iteration of the iterative process, the iterative process may also include generating, based on the at least one training sample, an estimated output using the machine learning model. For each iteration of the iterative process, the iterative process may further include obtaining an assessment result by assessing a difference between the estimated output and a reference output corresponding to the at least one training sample. For each iteration of the iterative process, the iterative process may include determining whether a termination condition is satisfied. In some embodiments, based on a determination whether the termination condition is satisfied, the iterative process may include updating, based on the assessment result, at least some of the parameter values of the machine learning model in response to the determination that the termination condition is not satisfied. Based on a determination whether the termination condition is satisfied, the iterative process may include designating the machine learning model with the parameter values updated in a last iteration as the trained machine learning model in response to the determination that the termination condition is satisfied.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not scaled. These embodiments are non-limiting exemplary embodiments, in which like reference numerals represent similar structures throughout the several views of the drawings, and wherein.

DETAILED DESCRIPTION

Figure 1:
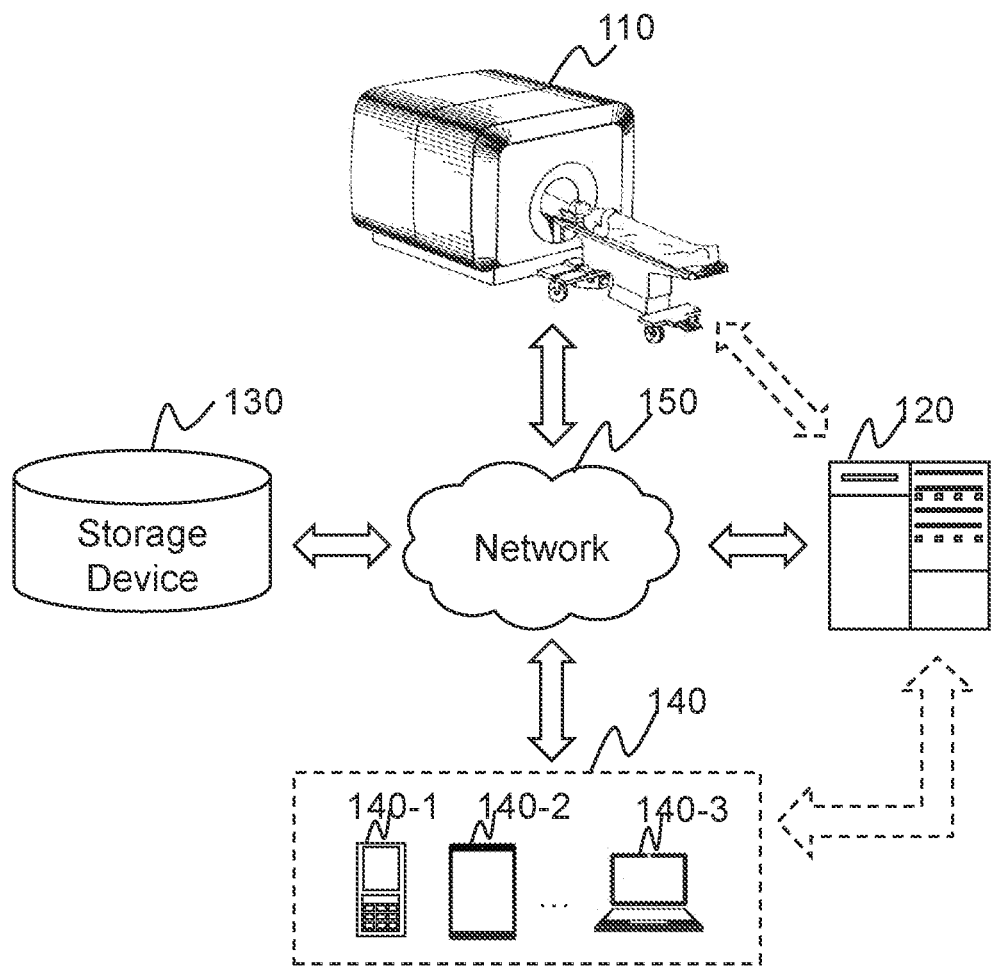
FIG. 1 is a schematic diagram illustrating an exemplary radiotherapy system according to some embodiments of the present disclosure.

The following description is presented to enable any person skilled in the art to make and use the present disclosure and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown but is to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including" when used in this disclosure, specify the presence of stated features, integers, steps, operations, elements, and/or components, but do not preclude the presence or addition of one or more other features, integers, steps, operations, elements, components, and/or groups thereof.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage devices. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an erasable programmable read-only memory (EPROM). It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that the term "system," "engine," "unit," "module," and/or "block" used herein are one method to distinguish different components, elements, parts, sections or assembly of different levels in ascending order. However, the terms may be displaced by another expression if they achieve the same purpose.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments in the present disclosure. It is to be expressly understood, the operations of the flowchart may be implemented not in order. Conversely, the operations may be implemented in an inverted order, or simultaneously. Moreover, one or more other operations may be added to the flowcharts. One or more operations may be removed from the flowcharts.

Provided herein are systems and methods for generating a dose distribution. A system may include at least one storage device storing executable instructions, and at least one processor in communication with the at least one storage device. When executing the executable instructions, the at least one processor may cause the system to obtain a first dose distribution in at least a portion of a subject. The at least one processor may also cause the system to obtain a trained machine learning model. The at least one processor may further cause the system to generate a second dose distribution in the at least a portion of the subject based on the first dose distribution and the trained machine learning model. The second dose distribution may include an accuracy higher than that of the first dose distribution. As the first dose distribution corresponding to the at least a portion of the subject is simulated under a small count of radiation particles, the computational speed for simulating the first dose distribution may be relatively high, but the accuracy of the first dose distribution may be low. The first dose distribution may be modified and adjusted using the trained machine learning model to improve the accuracy of the first dose distribution. Therefore, the modified first dose distribution (i.e., the second dose distribution) may have higher accuracy and fast computational speed, which can satisfy the actual clinical requirements.

FIG. 1 is a schematic diagram illustrating an exemplary radiotherapy system 100 according to some embodiments of the present disclosure. Merely by way of example, as illustrated in FIG. 1, the radiotherapy system 100 may include a radiation delivery device 110, a processing device 120, a storage device 130, one or more terminals 140, and a network 150. The components in the radiotherapy system 100 may be connected in one or more of various ways. Merely by way of example, the radiation delivery device 110 may be connected to the processing device 120 through the network 150. As another example, the radiation delivery device 110 may be connected to the processing device 120 directly as illustrated in FIG. 1. As a further example, the terminal(s) 140 may be connected to another component of the radiotherapy system 100 (e.g., the processing device 120) via the network 150. As still a further example, the terminal(s) 140 may be connected to the processing device 120 directly as illustrated by the dotted arrow in FIG. 1. As still a further example, the storage device 130 may be connected to another component of the radiotherapy system 100 (e.g., the processing device 120) directly as illustrated in FIG. 1, or through the network 150.

The radiation delivery device 110 may be a radiotherapy (RT) device. In some embodiments, the RT device may deliver one or more radiation beams to a treatment region (e.g., a tumor) of an object (e.g., a patient) for causing an alleviation of the object's symptom. In some embodiments, the RT device may be a conformal radiation therapy device, an image guided radiation therapy (IGRT) device, an intensity modulated radiation therapy (IMRT) device, an intensity modulated arc therapy (IMAT) device, or the like. In some embodiments, the RT device may include a linear accelerator (also referred to as "linac"). The linac may generate and emit a radiation beam (e.g., an X-ray beam) from a treatment head. The radiation beam may pass through one or more collimators (e.g., an MLC)) forming certain shapes, and enter into the object. In some embodiments, the radiation beam may include radiation particles, such as electrons, photons, or other types of radiation. In some embodiments, the energy of the radiation beam may be in the megavoltage range (e.g., >1 MeV), and may therefore be referred to as a megavoltage beam. The treatment head may be coupled to a gantry. The gantry may rotate, for example, clockwise or counter-clockwise around a gantry rotation axis. In some embodiments, the treatment head may rotate along with the gantry. In some embodiments, the RT device may further include a table configured to support the object during radiation treatment. In some embodiments, the RT device may perform treatment on the object according to a radiotherapy treatment plan of the object. In some embodiments, the radiotherapy treatment plan may be generated by a treatment planning system (TPS) associated with the radiotherapy system 100.

In some embodiments, the object to be treated or irradiated may include a body, substance, or the like, or any combination thereof. In some embodiments, the object may include a specific portion of a body, such as a head, a thorax, an abdomen, or the like, or any combination thereof. In some embodiments, the object may include a specific organ, such as a breast, an esophagus, a trachea, a bronchus, a stomach, a gallbladder, a small intestine, a colon, a bladder, a ureter, a uterus, a fallopian tube, etc.

The processing device 120 may process data and/or information obtained from the radiation delivery device 110, the terminal(s) 140, and/or the storage device 130. For example, the processing device 120 may obtain a first dose distribution in at least a portion of a subject. The processing device 120 may obtain a trained machine learning model. The processing device 120 may generate a second dose distribution in the at least a portion of the subject based on the first dose distribution and the trained machine learning model. The second dose distribution includes an accuracy higher than that of the first dose distribution. In some embodiments, the processing device 120 may input the first dose distribution into the trained machine learning model, and designate an output of the trained machine learning model as the second dose distribution. In some embodiments, the processing device 120 may input the first dose distribution into the trained machine learning model. The processing device 120 may generate a deviation between the first dose distribution and the second dose distribution using the trained machine learning model by processing the first dose distribution. The processing device 120 may determine the second dose distribution based on the first dose distribution and the deviation between the first dose distribution and the second dose distribution. In some embodiments, the processing device 120 may input the first dose distribution and personalized data of the subject into the trained machine learning model. The processing device 120 may determine the second dose distribution based on an output of the trained machine learning model.

The trained machine learning model used in the present disclosure (e.g., the trained machine learning model) may be updated from time to time, e.g., periodically or not, based on a sample set that is at least partially different from the original sample set from which the original trained machine learning model is determined. For instance, the trained machine learning model (e.g., the trained machine learning model) may be updated based on a sample set including new samples that are not in the original sample set. In some embodiments, the determination and/or updating of the trained machine learning model (e.g., the first trained machine learning model and/or second trained machine learning model) may be performed on a processing device, while the application of the trained machine learning model may be performed on a different processing device. In some embodiments, the determination and/or updating of the trained machine learning model (e.g., the trained machine learning model) may be performed on a processing device of a system different than the radiotherapy system 100 or a server different than a server including the processing device 120 on which the application of the trained machine learning model is performed. For instance, the determination and/or updating of the trained machine learning model (e.g., the trained machine learning model) may be performed on a first system of a vendor who provides and/or maintains such a machine learning model and/or has access to training samples used to determine and/or update the trained machine learning model, while the generation of the second dose distribution based on the provided machine learning model may be performed on a second system of a client of the vendor. In some embodiments, the determination and/or updating of the trained machine learning model (e.g., the trained machine learning model) may be performed online in response to a request for the generation of the second dose distribution. In some embodiments, the determination and/or updating of the trained machine learning model may be performed offline.

In some embodiments, the processing device 120 may be a computer, a user console, a single server or a server group, etc. The server group may be centralized or distributed. In some embodiments, the processing device 120 may be local or remote. For example, the processing device 120 may access information and/or data stored in the radiation delivery device 110, the terminal(s) 140, and/or the storage device 130 via the network 150. As another example, the processing device 120 may be directly connected to the radiation delivery device 110, the terminal(s) 140 and/or the storage device 130 to access stored information and/or data. In some embodiments, the processing device 120 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

The storage device 130 may store data, instructions, and/or any other information. In some embodiments, the storage device 130 may store data obtained from the terminal(s) 140 and/or the processing device 120. The data may include dose distribution data acquired by the processing device 120, algorithms and/or models for processing the dose distribution data, etc. For example, the storage device 130 may store dose distribution data (e.g., RT dose distribution data, IGRT dose distribution data, IMRT dose distribution data, etc.) acquired by the radiation delivery device 110. As another example, the storage device 130 may store one or more algorithms for processing the dose distribution data, a trained machine learning model for generation of the dose distribution, etc. In some embodiments, the storage device 130 may store data and/or instructions that the processing device 120 may execute or use to perform exemplary methods/systems described in the present disclosure. In some embodiments, the storage device 130 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memories may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 130 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 130 may be connected to the network 150 to communicate with one or more other components in the radiotherapy system 100 (e.g., the processing device 120, the terminal(s) 140, etc.). One or more components in the radiotherapy system 100 may access the data or instructions stored in the storage device 130 via the network 150. In some embodiments, the storage device 130 may be directly connected to or communicate with one or more other components in the radiotherapy system 100 (e.g., the processing device 120, the terminal(s) 140, etc.). In some embodiments, the storage device 130 may be part of the processing device 120.

The terminal(s) 140 may include a mobile device 140-1, a tablet computer 140-2, a laptop computer 140-3, or the like, or any combination thereof. In some embodiments, the mobile device 140-1 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 140 may be part of the processing device 120.

The network 150 may include any suitable network that can facilitate the exchange of information and/or data for the radiotherapy system 100. In some embodiments, one or more components of the radiation delivery device 110 (e.g., an RT device, a IGRT device, etc.), the terminal(s) 140, the processing device 120, the storage device 130, etc., may communicate information and/or data with one or more other components of the radiotherapy system 100 via the network 150. For example, the processing device 120 may obtain data from the radiation delivery device 110 via the network 150. As another example, the processing device 120 may obtain user instructions from the terminal(s) 140 via the network 150. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the radiotherapy system 100 may be connected to the network 150 to exchange data and/or information.

It should be noted that the above description of the radiotherapy system 100 is merely provided for the purposes of illustration, and not intended to limit the scope of the present disclosure. For persons having ordinary skills in the art, multiple variations and modifications may be made under the teachings of the present disclosure. For example, the assembly and/or function of the radiotherapy system 100 may be varied or changed according to specific implementation scenarios.

Figure 2:
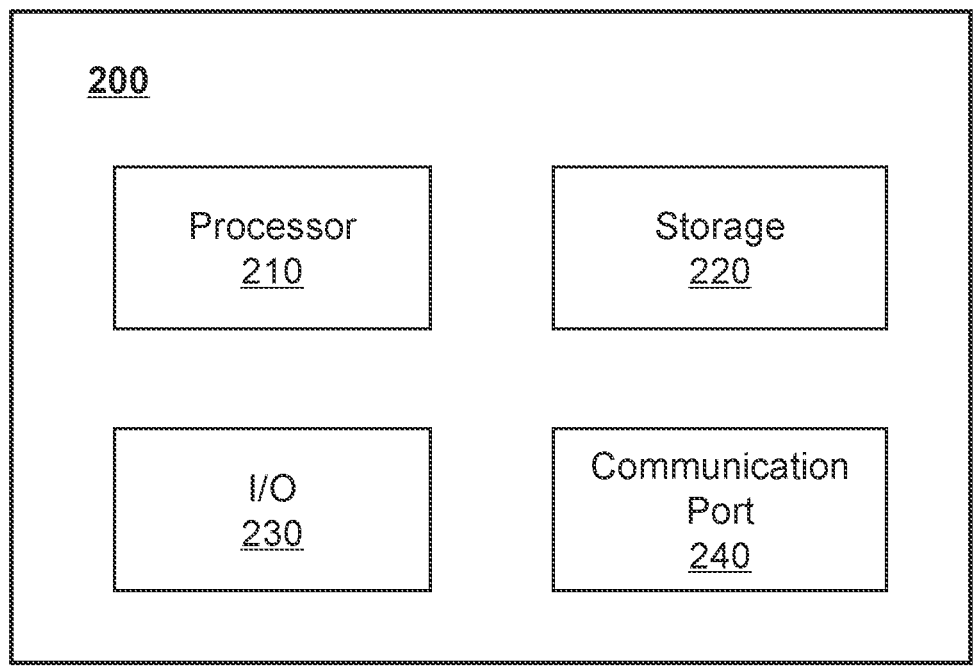
FIG. 2 is a schematic diagram illustrating hardware and/or software components of an exemplary computing device on which the processing device may be implemented according to some embodiments of the present disclosure.

FIG. 2 is a schematic diagram illustrating hardware and/or software components of an exemplary computing device 200 on which the processing device 120 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (program codes) and perform functions of the processing device 120 in accordance with techniques described herein. The computer instructions may include, for example, routines, programs, objects, components, signals, data structures, procedures, modules, and functions, which perform particular functions described herein. For example, the processor 210 may process data obtained from the radiation delivery device 110, the terminal(s) 140, the storage device 130, and/or any other component of the radiotherapy system 100. Specifically, the processor 210 may process one or more measured data sets obtained from the radiation delivery device 110. For example, the processor 210 may generate a second dose distribution based on the data set(s). In some embodiments, the generated second dose distribution may be stored in the storage device 130, the storage 220, etc. In some embodiments, the generated second dose distribution may be displayed on a display device by the I/O 230. In some embodiments, the processor 210 may perform instructions obtained from the terminal(s) 140. In some embodiments, the processor 210 may include one or more hardware processors, such as a microcontroller, a microprocessor, a reduced instruction set computer (RISC), an application-specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field-programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from the radiation delivery device 110, the terminal(s) 140, the storage device 130, or any other component of the radiotherapy system 100. In some embodiments, the storage 220 may include a mass storage device, a removable storage device, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the processing device 120 for generating a dose distribution data for a RT device.

The I/O 230 may input or output signals, data, and/or information. In some embodiments, the I/O 230 may enable user interaction with the processing device 120. In some embodiments, the I/O 230 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 240 may be connected with a network (e.g., the network 150) to facilitate data communications. The communication port 240 may establish connections between the processing device 120 and the radiation delivery device 110, the terminal(s) 140, or the storage device 130. The connection may be a wired connection, a wireless connection, or a combination of both that enables data transmission and reception. The wired connection may include an electrical cable, an optical cable, a telephone wire, or the like, or any combination thereof. The wireless connection may include a Bluetooth network, a Wi-Fi network, a WiMax network, a WLAN, a ZigBee network, a mobile network (e.g., 3G, 4G, 5G, etc.), or the like, or any combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
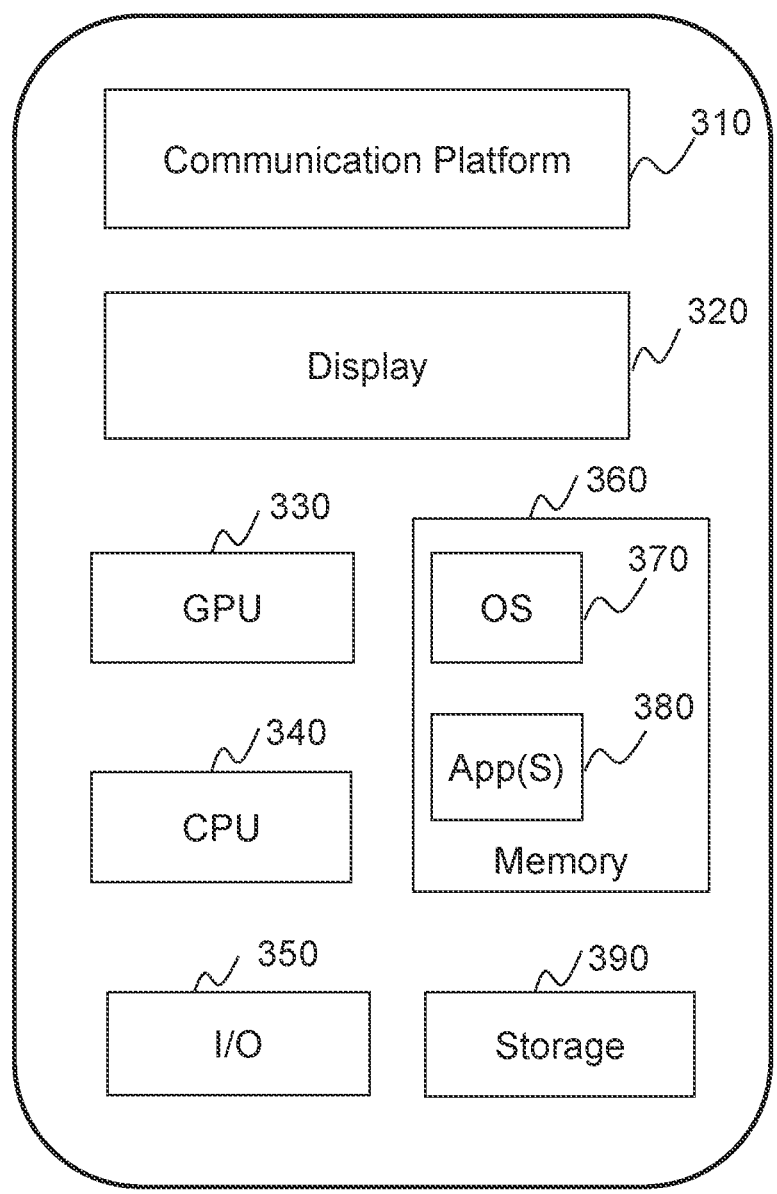
FIG. 3 is a schematic diagram illustrating hardware and/or software components of an exemplary mobile device according to some embodiments of the present disclosure.

FIG. 3 is a schematic diagram illustrating hardware and/or software components of an exemplary mobile device 300 according to some embodiments of the present disclosure. As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS, Android, Windows Phone, etc.) and one or more applications 380 may be loaded into the memory 360 from the storage 390 in order to be executed by the CPU 340. The applications 380 may include a browser or any other suitable mobile apps for receiving and rendering information relating to dose distribution processing or other information from the processing device 120. User interactions with the information stream may be achieved via the I/O 350 and provided to the processing device 120 and/or other components of the radiotherapy system 100 via the network 150.

To implement various modules, units, and functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to generate a dose distribution as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result, the drawings should be self-explanatory.

Figure 4A:
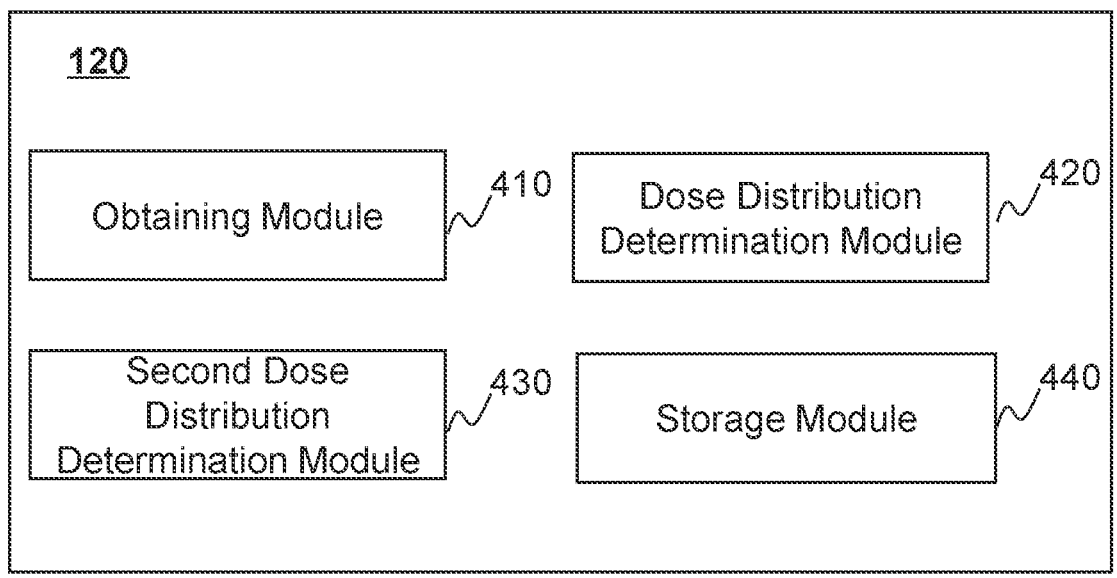
FIG. 4A is a block diagram illustrating an exemplary processing device according to some embodiments of the present disclosure.

FIG. 4A is a block diagram illustrating an exemplary processing device according to some embodiments of the present disclosure. In some embodiments, processing device 120 may be implemented on a computing device 200 (e.g., the processor 210) illustrated in FIG. 2 or a CPU 340 as illustrated in FIG. 3. As illustrated in FIG. 4A, the processing device 120 may include an obtaining module 410, a dose distribution determination module 420, a second dose distribution determination module 430, and a storage module 440. Each of the modules described above may be a hardware circuit that is designed to perform certain actions, e.g., according to a set of instructions stored in one or more storage media, and/or any combination of the hardware circuit and the one or more storage media.

The obtaining module 410 may be configured to obtain data and/or information for computing a dose distribution. For example, the obtaining module 410 may obtain personalized data of a subject. The personalized data of the subject may refer to information and/or data of the subject that is used to compute and/or simulate a dose distribution in different portions of the subject. The personalized data of the subject may include a radiotherapy treatment plan of the subject, a density distribution in the subject, or the like, or any combination thereof. The radiotherapy treatment plan of the subject may refer to data that is used to treat the subject in a radiotherapy equipment (e.g., the radiation delivery device 110, e.g., an electron linac). As another example, the obtaining module 410 may obtain a trained machine learning model. As still another example, the obtaining module 410 may obtain a particle transport model. In some embodiments, the particle transport model may be established based on a physical process of particle transport.

The dose distribution determination module 420 may be configured to determine a dose distribution in at least a portion of a subject. The dose distribution in a specific subject may describe absorption levels of different portion or positions of the specific subject to radiation or radiation energy. For example, the dose distribution determination module 420 may determine a dose distribution (e.g., the first dose distribution) in at least a portion of a subject based on the personalized data of the subject using a simulation technique. As another example, the dose distribution determination module 420 may obtain a corresponding relationship between the computational speed for simulating a dose distribution and the count of radiation particles that are used to simulate the dose distribution. The dose distribution determination module 420 may determine a count of radiation particles that are used to simulate the dose distribution based on the computational speed. As still another example, the dose distribution module 420 may generate the count of radiation particles based on data of initial radiation particles and a radiotherapy treatment plan of a subject.

The second dose distribution determination module 430 may be configured to generate a second dose distribution in the at least a portion of the subject based on a first dose distribution and the trained machine learning model. The second dose distribution may include an accuracy higher than that of the first dose distribution. For example, the second dose distribution generation module 430 may input the first dose distribution into the trained machine learning model, and designate an output of the trained machine learning model as the second dose distribution. As another example, the second dose distribution generation module 430 may input the first dose distribution into the trained machine learning model. The trained machine learning model may generate and/or output a deviation between the first dose distribution and the second dose distribution by processing the first dose distribution. The second dose distribution generation module 430 may determine the second dose distribution based on the first dose distribution and the deviation between the first dose distribution and the second dose distribution.

The storage module 440 may be configured to store data and/or instructions associated with the radiotherapy system 100. For example, the storage module 440 may store data of the personalized data of the subject, the second dose distribution, the second dose distribution, the trained machine learning model, etc. In some embodiments, the storage module 440 may be the same as the storage device 130 and/or the storage module 470 in the configuration.

It should be noted that the above description is merely provided for the purposes of illustration, and not intended to limit the scope of the present disclosure. Apparently, for persons having ordinary skills in the art, multiple variations and modifications may be conducted under the teachings of the present disclosure. However, those variations and modifications do not depart from the scope of the present disclosure. For example, the dose distribution determination module 420 and the second dose distribution determination module 430 may be integrated into a single module. As another example, some other components/modules may be added into the processing device 120.

Figure 4B:
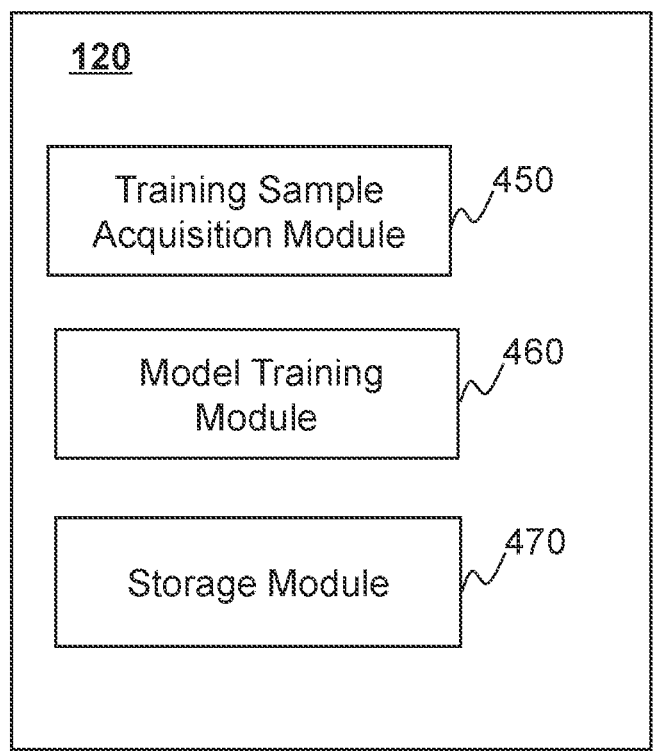
FIG. 4B is a block diagram illustrating an exemplary processing device according to some embodiments of the present disclosure.

FIG. 4B is a block diagram illustrating an exemplary processing device according to some embodiments of the present disclosure. In some embodiments, processing device 120 may be implemented on a computing device 200 (e.g., the processor 210) illustrated in FIG. 2 or a CPU 340 as illustrated in FIG. 3. As illustrated in FIG. 4B, the processing device 120 may include a training sample acquisition module 450, a model training module 460, and a storage module 470. Each of the modules described above may be a hardware circuit that is designed to perform certain actions, e.g., according to a set of instructions stored in one or more storage media, and/or any combination of the hardware circuit and the one or more storage media.

The obtaining module 450 may be configured to obtain a plurality of training samples. The plurality of training samples may refer to data configured to train the machine learning model. For example, each of the plurality of training samples may include a third dose distribution with low accuracy and a fourth dose distribution with high accuracy in a specific object. The fourth dose distribution may serve as a reference output (i.e., a desired output) of the machine learning model, and the third dose distribution and the personalized data may serve as an input of the machine learning model. As another example, each of the plurality of training samples may include the third dose distribution of a specific object and a difference between the third dose distribution and the fourth dose distribution of the specific object. The difference between the third dose distribution and the fourth dose distribution may serve as the reference output of the machine learning model in the iterative process and the third dose distribution may serve as an input of the machine learning model.

The model training module 460 may be configured to train the machine learning model by the plurality of training samples. In some embodiments, the model training module 460 may construct the trained machine learning model based on a convolutional neural network (CNN) model, a recurrent neural network (RNN) model, a long short term memory (LSTM) network model, a fully convolutional neural network (FCN) model, a generative adversarial network (GAN) model, a back propagation (BP) machine learning model, a radial basis function (RBF) machine learning model, a deep belief nets (DBN) machine learning model, an Elman machine learning model, or the like, or any combination thereof. The model training module 460 may train the machine learning model based on the plurality of training samples using a training algorithm. In some embodiments, the model training module 460 may perform a plurality of iterations to iteratively update one or more parameter values of the machine learning model to obtain the trained machine learning model. Before the plurality of iterations, the model training module 460 may initialize the parameter values of the machine learning model.

The storage module 470 may be configured to store data and/or instructions associated with the radiotherapy system 100. For example, the storage module 440 may store data of the plurality of training samples (e.g., the third dose distribution with low accuracy and the fourth dose distribution with high accuracy in a specific object), one or more machine learning models, the trained machine learning model, etc. In some embodiments, the storage module 470 may be the same as the storage device 130 and/or the storage module 440 in the configuration.

It should be noted that the above description is merely provided for the purposes of illustration, and not intended to limit the scope of the present disclosure. Apparently, for persons having ordinary skills in the art, multiple variations and modifications may be conducted under the teachings of the present disclosure. However, those variations and modifications do not depart from the scope of the present disclosure. For example, the training sample acquisition module 450 and the storage module 470 may be integrated into a single module. As another example, some other components/modules may be added into the processing device 120.

Figure 5:
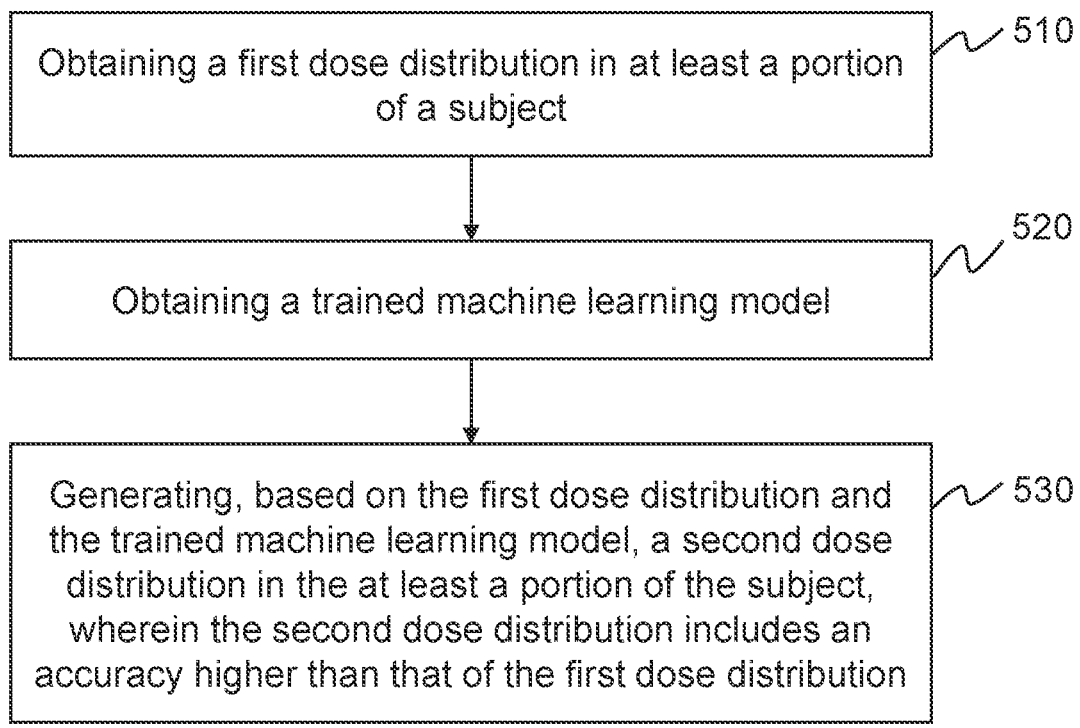
FIG. 5 is a schematic flowchart illustrating an exemplary process for generating a dose distribution according to some embodiments of the present disclosure.

FIG. 5 is a schematic flowchart illustrating an exemplary process for generating a dose distribution according to some embodiments of the present disclosure. In some embodiments, process 500 may be implemented as a set of instructions (e.g., an application) stored in the storage device 130, storage 220, or storage 390. The processing device 120, the processor 210 and/or the CPU 340 may execute the set of instructions, and when executing the instructions, the processing device 120, the processor 210 and/or the CPU 340 may be configured to perform the process 500. The operations of the illustrated process presented below are intended to be illustrative. In some embodiments, the process 500 may be accomplished with one or more additional operations not described and/or without one or more of the operations discussed. Additionally, the order of the operations of the process 500 illustrated in FIG. 5 and described below is not intended to be limiting.

In 510, the processing device 120 (e.g., the obtaining module 410 and/or dose distribution determination module 420) may obtain a first dose distribution in at least a portion of a subject. In some embodiments, the subject may be an object to be treated or irradiated that includes a body, substance, or the like, or any combination thereof. In some embodiments, the object may include a specific portion of a body, such as a head, a thorax, an abdomen, or the like, or any combination thereof. In some embodiments, the object may include a specific organ, such as a breast, an esophagus, a trachea, a bronchus, a stomach, a gallbladder, a small intestine, a colon, a bladder, a ureter, a uterus, a fallopian tube, etc. As used herein, a dose distribution in a specific subject may describe absorption levels of different portions or positions of the specific subject to radiation (or radiation energy). The absorption level of a portion of the specific subject may be denoted by an absorbed dose, an absorbed dose rate, etc. A dose distribution may be also referred to as a radiation dose distribution. In some embodiments, the first dose distribution may describe a distribution of a first count of radiation particles in different positions of the at least a portion of the subject. In other words, the first dose distribution may describe absorption levels of different positions of the at least a portion of the subject to the first count of radiation particles. In some embodiments, the first count may be less than a threshold. The threshold may be set by a user (e.g., a doctor, a radiologist, an operator of a radiotherapy device, an expert of a radiotherapy device, or the like) or according to a default setting of the radiotherapy system 100. For example, the threshold may be set based on an operational constraint of the radiotherapy system 100. The operational constraint may include a computing speed or time for the processing device 120 to simulate the first dose distribution. The greater the computing speed is, the smaller the threshold may be. In some embodiments, the processing device 120 may obtain a relationship between the computing speed and the threshold or particle count. The processing device 120 may determine the first particle count based on the relationship between the computing speed and the threshold or particle count. In some embodiments, the threshold may be a constant, such as $10^5$, $10^6$, $10^7$, $10^8$, or the like.

In some embodiments, the processing device 120 (e.g., the obtaining module 410) may determine and/or simulate the first dose distribution based on personalized data of the subject. The personalized data of the subject may be obtained from the storage device 130, the terminals 140, or any other system (e.g., a treatment planning system (TPS)) or storage. The personalized data of the subject may refer to information and/or data of the subject that is used to compute and/or simulate a dose distribution in different portions of the subject. In some embodiments, the personalized data of the subject may include a radiotherapy treatment plan of the subject, a density distribution in the subject, or the like, or any combination thereof. In some embodiments, the radiotherapy treatment plan of the subject may refer to data that is used to treat the subject (e.g., the radiation delivery device 110, e.g., an electron linac). In some embodiments, the radiotherapy treatment plan may include a value of an energy of a particle source (i.e., a radiation source) for generating radiation, penetration depth information of radiation particles in the subject, an angle of a gantry of a radiation device, a shape of a radiation field collimated by a collimator (e.g., a multi-leaf collimator, a Y-JAW, X-JAW, etc.), a radiation dose outputted by the radiation device, or the like, or any combination thereof. In some embodiments, the density distribution in the subject may be configured to characterize densities of different portions of the subject (such as a tissue, an organ, or the like). In some embodiments, the density distribution in the subject may be obtained according to image data of the subject. The image data (e.g., an image) of the subject may present structural information of the subject. In some embodiments, the image data of the subject may be obtained by an imaging device via scanning the subject. The image data may include, but not limited to, a CT image, an MR image, a PET image, an infrared image, a visible light image, or the like, or any combination thereof. In some embodiments, the CT image and the MR image may be anatomical structure images of the subject acquired by a CT device and an MR device, respectively scanning the subject, while the infrared images and the visible images may be generated using a model or human body model through deformation according to the contour of the subject. In some embodiments, the imaging device may include a simulator. As used herein, the simulator may refer to a scanning device or system used in the process of virtual simulation positioning and designing a radiotherapy treatment plan before radiotherapy treatment. For example, the simulator may include a CT (computed tomography) simulator, an MR (magnetic resonance imaging) simulator, etc. The processing device 120 may transform the image data into an image representing the density distribution of the subject.

The radiotherapy treatment plan may be determined based on the image representing the density distribution of the subject. For example, a target area and an endangered region (e.g., an organ surrounding the target area) of the subject may be sketched on the image representing the density distribution of the subject by the user using the treatment planning system (TPS), so as to generate the radiotherapy treatment plan corresponding to the subject. In some embodiments, the target area may refer to a tumor area that needs radiotherapy treatment, and the endangered region may refer to an area, such as an eyeball, the heart, a lung, etc., that cannot receive or be exposed to a high radiation dose during the radiotherapy treatment.

In some embodiments, the processing device 120 (e.g., the dose distribution determination module 420) may determine the first dose distribution in the at least a portion of the subject based on the personalized data of the subject using a simulation technique. Exemplary simulation techniques may include a Monte Carlo algorithm, a greedy algorithm, a dynamic programming algorithm, a divide-and-conquer algorithm, a backtracking algorithm, a branch bound algorithm, a pencil beam algorithm, a cone convolution algorithm, or the like, or any combination thereof. More descriptions for obtaining the first dose distribution may be found in FIG. 6 and the descriptions thereof.

In some embodiments, after determination, the processing device 120 (e.g., the storage module 440) may store the first dose distribution in the at least a portion of the subject in one or more storage devices (e.g., the storage device 130, the storage 220, and/or the storage 390) of the radiotherapy system 100 and/or an external data source. Therefore, the processing device 120 may obtain the first dose distribution from the storage device(s) or the external data source.

In 520, the processing device 120 (e.g., the obtaining module 410) may obtain a trained machine learning model. In some embodiments, the trained machine learning model may provide a first mapping relationship between a dose distribution corresponding to a low count of radiation particles (or a low radiation energy) in a specific object and a dose distribution corresponding to a high count of radiation particles (or a high radiation energy) in the specific object with respect to the low count of radiation particles. The trained machine learning model may be used to determine the dose distribution corresponding to the high count of radiation particles (or a high radiation energy) in the specific object based on the first mapping relationship and the dose distribution corresponding to the low count of radiation particles (or a low radiation energy) in the specific object. In some embodiments, the trained machine learning model may provide a second mapping relationship between a dose distribution corresponding to a low count of radiation particles (or a low radiation energy) in a specific object and a deviation between a dose distribution corresponding to a high count of radiation particles (or a high radiation energy) in the specific object and the dose distribution corresponding to the low count of radiation particles. The trained machine learning model may be used to determine the deviation between the dose distribution corresponding to the high count of radiation particles (or a high radiation energy) in the specific object and the dose distribution corresponding to the low count of radiation particles based on the second mapping relationship and the dose distribution corresponding to the low count of radiation particles (or a low radiation energy) in the specific object.

In some embodiments, the trained machine learning model may be a personalized trained machine learning model that is adapted to the subject as described in operation 510. The personalized trained machine learning model may be obtained by a processing device different or same as the processing device 120 via training a machine learning model using a plurality of training samples determined based on the personalized data of the subject as described in 510. In some embodiments, the trained machine learning model may be a generalized trained machine learning model that is adapted to different objects. The generalized trained machine learning model may be obtained by a processing device different or same as the processing device 120 via training a machine learning model using a plurality of training samples determined based on personalized data of multiple objects. More descriptions for the personalized trained machine learning model and the generalized trained machine learning model may be found in FIG. 8 and the descriptions thereof.

In some embodiments, the trained machine learning model may be a predetermined machine learning model with supervised learning or unsupervised learning. In some embodiments, the trained machine learning model may be obtained by training a machine learning model using the plurality of training samples. In some embodiments, each of the plurality of training samples may include a third dose distribution with low accuracy and a fourth dose distribution with high accuracy in a specific object. The third dose distribution and the fourth dose distribution corresponding to the same object may be designated as a training sample. The third dose distribution may describe a distribution of a third count of radiation particles (also referred to as third particle count) of different positions of the specific object. The fourth dose distribution may describe a distribution of a fourth count of radiation particles (also referred to as fourth particle count) of different positions of the subject. The fourth count may exceed the third count such that the fourth dose distribution has a higher accuracy than that of the third dose distribution. In some embodiments, each of the plurality of training samples may include the third dose distribution of a specific object and a difference between the third dose distribution and the fourth dose distribution of the specific object. In some embodiments, each of the plurality of training samples may be determined based on personalized data of a specific object using a simulation technique. At least two of the plurality of training samples may be determined using the same simulation technique or different simulation techniques. The third dose distribution and the fourth dose distribution corresponding to at least one of the plurality of training samples may be determined based on personalized data of a specific object using the same simulation technique or different simulation techniques. In some embodiments, the trained machine learning model may be generated by iteratively updating parameter values of a machine learning model based on the plurality of training samples in a training process. More descriptions of a training process may be found in FIG. 7 and the descriptions thereof.

In some embodiments, after the processing device different or same as the processing device 120 generates the trained machine learning model online or offline, the processing device different or same as the processing device 120 (e.g., the storage module 440) may store the trained machine learning model in one or more storage devices (e.g., the storage device 130, the storage 220, and/or the storage 390) of the radiotherapy system 100 and/or an external data source. Therefore, the processing device 120 may obtain the trained machine learning model from the storage device(s) or the external data source.

In 530, the processing device 120 (e.g., the second dose distribution generation module 430) may generate the second dose distribution in the at least a portion of the subject based on the first dose distribution and the trained machine learning model. In some embodiments, the second dose distribution may include an accuracy higher than that of the first dose distribution. As used herein, a dose distribution that is simulated based on a simulation technique may be also referred to as a simulated dose distribution. The accuracy of a dose distribution may also be referred to as a simulation accuracy. The simulation accuracy of a simulated dose distribution may be used to describe a deviation between the simulated dose distribution corresponding a count of radiation particles and an actual dose distribution generated when a subject receives or exposure to the count of radiation particles. The greater the simulation accuracy is, the smaller the deviation may be. The second dose distribution may describe a distribution of a second count of radiation particles (also referred to as second particle count) of different positions of the at least a portion of the subject. In other words, the second dose distribution may describe absorption levels of different positions of the at least a portion of the subject to the second count of radiation particles. The second count may exceed the first count, such that the second dose distribution may include an accuracy higher than that of the first dose distribution. As used herein, radiation particles that are used to simulate a dose distribution using a simulation technique may also be referred to as simulation radiation particles. The count of simulation radiation particles that are used to simulate a dose distribution may also be referred to as a simulation count of radiation particles. For example, the radiation particles that are used to simulate the first dose distribution may also referred to as first simulation radiation particles. The first count may also be referred to as a first equivalent count. Radiation particles that are used to describe a dose distribution generated using a trained machine learning model may also be referred to as equivalent radiation particles that are needed to simulate the dose distribution using a simulation technique. The count of equivalent radiation particles may also be referred to as an equivalent count of equivalent radiation particles. For example, radiation particles that are used to describe the second dose distribution generated using the trained machine learning model may also be referred to as second equivalent radiation particles. The second count may also be referred to as a second equivalent count.

In some embodiments, the processing device 120 (e.g., the second dose distribution generation module 430) may input the first dose distribution into the trained machine learning model, and designate an output of the trained machine learning model as the second dose distribution. In some embodiments, the processing device 120 (e.g., the second dose distribution generation module 430) may input the first dose distribution into the trained machine learning model. The trained machine learning model may generate and/or output a deviation between the first dose distribution and the second dose distribution by processing the first dose distribution. The processing device 120 may determine the second dose distribution based on the first dose distribution and the deviation between the first dose distribution and the second dose distribution. In some embodiments, the deviation may also be referred to as a dose distribution error of the first dose distribution calculated using a simulation technique. In some embodiments, the trained machine learning model for generating the deviation between the first dose distribution and the second dose distribution may be also referred to as a dose distribution error model, that is, the trained machine learning model may be used to calculate the dose distribution error of the inputted first dose distribution, thereby real-time monitoring of the deviation of the first dose distribution determined using the simulation technique, e.g., the Monte Carlo algorithm. Specifically, the deviation of the first dose distribution outputted by the trained machine learning model may be superimposed with the first dose distribution. The superimposed result may be designated as the second dose distribution with higher accuracy corresponding to the subject, which may improve the accuracy of the first dose distribution, thereby achieving improved radiotherapy effect. In some embodiments, the output result of the trained machine learning model may be directly set as the second dose distribution with higher accuracy, so that the output result of the trained machine learning model can be directly designated as the second dose distribution corresponding to the subject, thereby further improving the computational speed of the second radiation dose. In some embodiments, the processing device 120 (e.g., the second dose distribution generation module 430) may input the first dose distribution and the personalized data of the subject into the trained machine learning model, and determine the second dose distribution based on an output of the trained machine learning model.

In some embodiments, if a dose distribution in a specific object is simulated based on a high count of radiation particles (or high radiation energy) using a simulation technique (e.g., the Monte Carlo algorithm), the accuracy of the dose distribution may be high but the computational speed may be low. If a dose distribution in a specific object is simulated based on a low count of radiation particles (or low radiation energy) using a simulation technique (e.g., the Monte Carlo algorithm), the accuracy of the dose distribution may be low but the computational speed may be high. In the present disclosure, the first dose distribution may be determined based on the low count of radiation particles using a simulation technique, therefore the computational speed may be high. And then the second dose distribution under the high count of radiation particles may be obtained based on the first dose distribution using the trained machine learning model, thereby improving the accuracy of the second dose distribution on the premise of improving the computational speed.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be omitted and/or one or more additional operations may be added. For example, operation 510 and operation 520 may be combined into a single operation. As another example, one or more other optional operations (e.g., a storing operation) may be added elsewhere in the process 500. In the storing operation, the processing device 120 may store information and/or data (e.g., the first dose distribution, the second dose distribution, the trained machine learning model, etc.) associated with the radiotherapy system 100 in a storage device (e.g., the storage device 130) disclosed elsewhere in the present disclosure.

Figure 6:
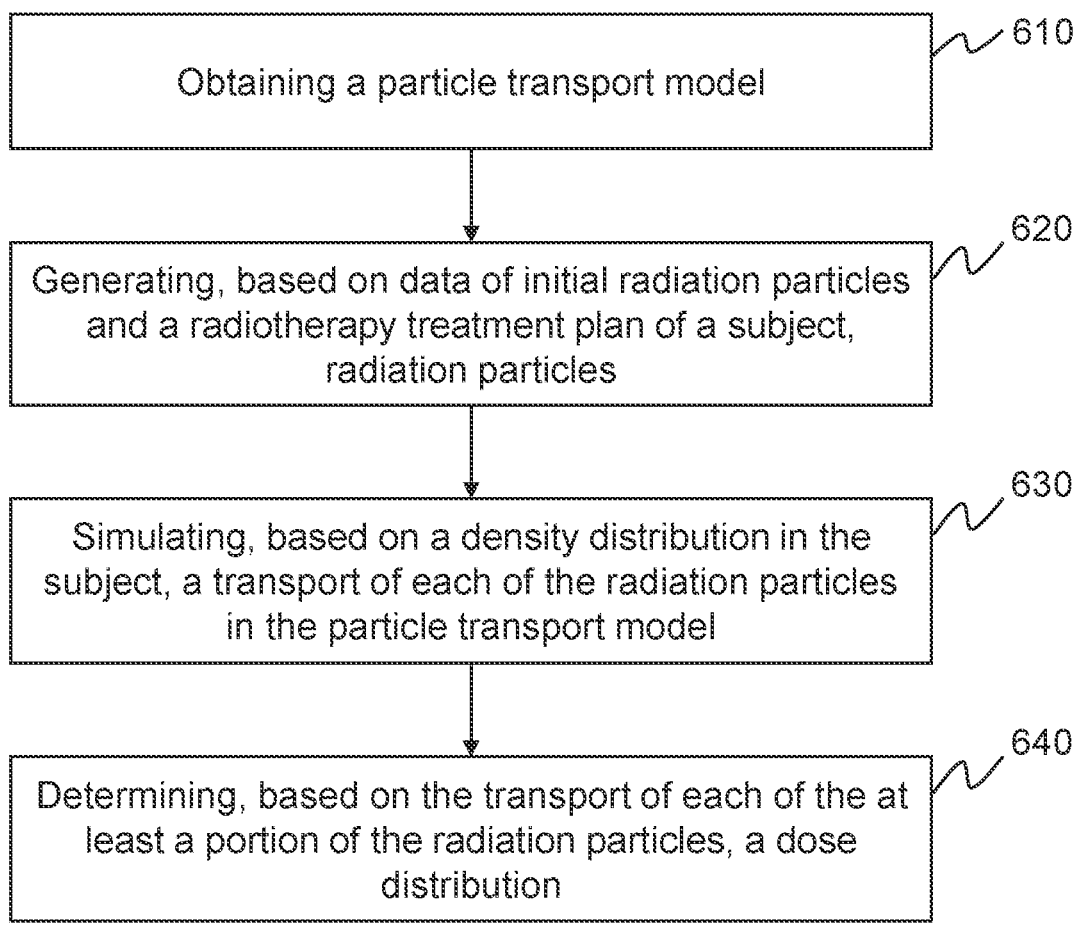
FIG. 6 is a schematic flowchart illustrating an exemplary process for generating a dose distribution according to some embodiments of the present disclosure.

FIG. 6 is a schematic flowchart illustrating an exemplary process for generating a dose distribution according to some embodiments of the present disclosure. In some embodiments, process 600 may be implemented as a set of instructions (e.g., an application) stored in the storage device 130, storage 220, or storage 390. The processing device 120, the processor 210 and/or the CPU 340 may execute the set of instructions, and when executing the instructions, the processing device 120, the processor 210 and/or the CPU 340 may be configured to perform the process 600. The operations of the illustrated process presented below are intended to be illustrative. In some embodiments, the process 600 may be accomplished with one or more additional operations not described and/or without one or more of the operations discussed. Additionally, the order of the operations of process 600 illustrated in FIG. 6 and described below is not intended to be limiting. In some embodiments, the first dose distribution described in connection with operation 510 in FIG. 5 may be obtained according to the process 600. In some embodiments, a dose distribution may refer to expected values of energy deposition of a plurality of random or pseudo-random radiation particles in different grid elements during particle transport. In some embodiments, a Monte Carlo algorithm may be used to compute the dose distribution.

In 610, the processing device 120 (e.g., the obtaining module 410) may obtain a particle transport model. In some embodiments, the particle transport model may be established based on a physical process of particle transport. In some embodiments, the physical process may be defined and/or described by a shape of a phantom (e.g., a cube shape, a cylinder shape, a cuboid shape, etc.), a material (e.g., tungsten, lead, gold, palladium, or the like, or any combination thereof) of a radiation source, a distribution of particle sources (e.g., photons, electrons, positrons), a distribution of next collision points, a probability of each collision, a type of each collision, an energy distribution after reaction between radiation particles and a subject to be simulated, an angle of a moving direction of radiation particles after the reaction between radiation particles and a subject to be simulated, a condition at which radiation particle ends the motion, a physical quantity determined of the transport simulation, or the like. In some embodiments, the particle transport model may be obtained based on all the physical processes of each radiation particle in the particle described by a transport function. Exemplary transport functions may include a direct simulation approach, a weighted approach, a statistical estimation approach, or the like.

In 620, the processing device 120 (e.g., the dose distribution module 420) may generate radiation particles based on data of initial radiation particles and a radiotherapy treatment plan of a subject. In some embodiments, before generating the radiation particles, the processing device 120 may determine the count (e.g., the first count as described in FIG. 5) of the radiation particles. The count of the radiation particles used to simulate a dose distribution may be set by a user or according to a default setting of the radiotherapy system 100. For example, the count of the radiation particles (e.g., the second count as described in FIG. 5) may exceed to a threshold. As another example, the count of the radiation particles (e.g., the first count as described in FIG. 5) may be less than a threshold. In some embodiments, the count of the radiation particles may be determined according to a corresponding relationship between the count of radiation particles and the computational speed for the processing device 120 simulating a dose distribution corresponding to the count of the radiation particles. For example, the processing device 120 may obtain the corresponding relationship and the computational speed from the storage device 130. The computational speed may be determined based on clinical demands. Then the processing device 120 may determine the count of the radiation particles based on the corresponding relationship and the computational speed. In some embodiments, the count of radiation particles may be a constant, such as $10^7$, $2 \times 10^7$, $3 \times 10^7$, etc.

In some embodiments, the data of initial radiation particles may include a distribution of the initial radiation particles, such as a position distribution of the initial radiation particles, an energy distribution of the initial radiation particles, a motion direction distribution of the initial radiation particles, etc. In some embodiments, the position distribution of the initial radiation particles may include a uniform distribution within a circle, a uniform distribution within a circular ring, a uniform distribution within a sphere, a uniform distribution within a spherical shell, a uniform distribution within a cylinder, a point source distribution, a distribution of parallel beam sources outside a sphere, or the like, or any combination thereof. In some embodiments, the energy distribution of the initial radiation particles may include a single energy distribution, a fission neutron spectrum distribution, a Maxwell spectrum distribution, or the like, or any combination thereof. In some embodiments, the motion direction distribution of the initial radiation particles may include an isotropic distribution, a half-surface isotropic distribution, an extra-spherical beam source distribution, an extra-spherical isotropic point source distribution, or the like, or any combination thereof.

In some embodiments, the processing device 120 may randomly or pseudo-randomly sample the radiation particles from the initial radiation particles using a sampling algorithm. The sampling algorithm may include a particle filter resampling, a sampling importance resampling, a sequential importance resampling, a self-adaptive linear resampling, etc. In some embodiments, the sampling algorithm may be determined according to the data of initial radiation particles. For example, if the count of the initial radiation particles used to simulate the dose distribution exceeds a threshold, the sequential importance resampling may be used. While the count of the initial radiation particles is less than a threshold, the sampling importance resampling may be used. The processing device 120 may sample the radiation particles based on the radiotherapy treatment plan of the subject. Then the data of radiation particles may be obtained. The data of radiation particles may include a spatial position distribution of the radiation particles, an energy distribution of the radiation particles, a motion direction distribution of the radiation particles, etc. The radiotherapy treatment plan of the subject may include a value of an energy of a particle source (i.e., a radiation source), a penetration depth of radiation particles in the subject, an angle of a gantry of a radiation device, a shape of a radiation field collimated by a collimator, a radiation dose outputted by the radiation device, or the like, or any combination thereof. For example, the processing device 120 may sample the radiation particles whose energy distribution of the radiation particles satisfies the value of the energy of the particle source (i.e., a radiation source) and/or the radiation dose outputted by the radiation device included in the radiotherapy treatment plan. As another example, the processing device 120 may sample the radiation particles whose spatial position distribution and the motion direction distribution match the penetration depth of radiation particles in the subject, the angle of a gantry of a radiation device, the shape of a radiation field collimated by the collimator included in the radiotherapy treatment plan.

In 630, the processing device 120 (e.g., the dose determination module 420) may simulate a transport of each of the radiation particles in the particle transport model based on a density distribution in the subject. The density distribution in the subject may be configured to characterize densities of different portions of the subject (such as a tissue, an organ, or the like). In some embodiments, the density distribution in the subject may be obtained according to image data of the subject. More descriptions of the density distribution in the subject may be found in FIG. 5 and the descriptions thereof. In some embodiments, during the transport simulation process, the transport of each of the radiation particles may be simulated according to a reaction cross-section database. The reaction cross-section may refer to a probability of a nuclear reaction of a specific type happens between a radiation particle and a target nucleus. The reaction cross-section database may be a database including probabilities of nuclear reactions of different types happen between radiation particles and the target nucleus. The reaction cross-section database may be used to determine a reacting mechanism of the radiation particles and the particle transport model during the transport process. For example, the reaction mechanism of photons and atoms may include the photoelectric effect, the Compton scattering, the electron pair generation, the Rayleigh scattering, or the like, or any combination thereof. As another example, the reaction mechanism of electrons and substances may include the multiple scattering, the bremsstrahlung, the positron quiescence annihilation, the positron flight annihilation, or the like, or any combination thereof. In some embodiments, in the transport of the radiation particles, the radiation particles may interact with the particle transport model. Secondary particles may be generated after nuclear reactions happen between the radiation particles and the transport model. The processing device 120 may determine the types of nuclear reactions happening between the radiation particles and the particle transport model according to the reaction cross-section database. Data associated with the secondary particles may be determined based on the types of nuclear reactions happening between the radiation particles and the particle transport model. The secondary particles may be randomly or pseudo-randomly sampled. The sampled secondary particles may be further transported in the particle transport model according to the data associated with the sampled secondary particles, such as the spatial position distribution of the sampled secondary particles the energy distribution of the sampled secondary particles, the direction distribution of the sampled secondary particles, etc.

In 640, the processing device 120 (e.g., the dose distribution determination module 420) may determine a dose distribution in the subject based on the transport of each of the at least a portion of the radiation particles. In some embodiments, the result of the transport of each of the at least a portion of the radiation particles may include different desired values of the energy of radiation particles including the secondary particles deposited in different grid elements. The grid elements may represent different portions of the subject. The dose distribution may be determined based on the result of the transport. The computational speed for simulating the dose distribution is related to the count of the radiation particles. The greater the count of the radiation particles is, the smaller the computational speed may be. The dose distribution corresponding to the low count of radiation particles may be quickly determined.

In some embodiments, after obtaining the dose distribution, the processing device 120 (e.g., the storage module 440) may store the dose distribution in one or more storage devices (e.g., the storage device 130, the storage 220, and/or the storage 390) of the radiotherapy system 100 and/or an external data source. Therefore, the processing device 120 may obtain the dose distribution from the storage device(s) or the external data source.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be omitted and/or one or more additional operations may be added. For example, operation 620 and operation 630 may be combined into a single operation. As another example, one or more other optional operations (e.g., a storing operation) may be added elsewhere in the process 600. In the storing operation, the processing device 120 may store information and/or data (e.g., the particle transport model, reaction cross-section database, etc.) associated with the radiotherapy system 100 in a storage device (e.g., the storage device 130) disclosed elsewhere in the present disclosure.

Figure 7:
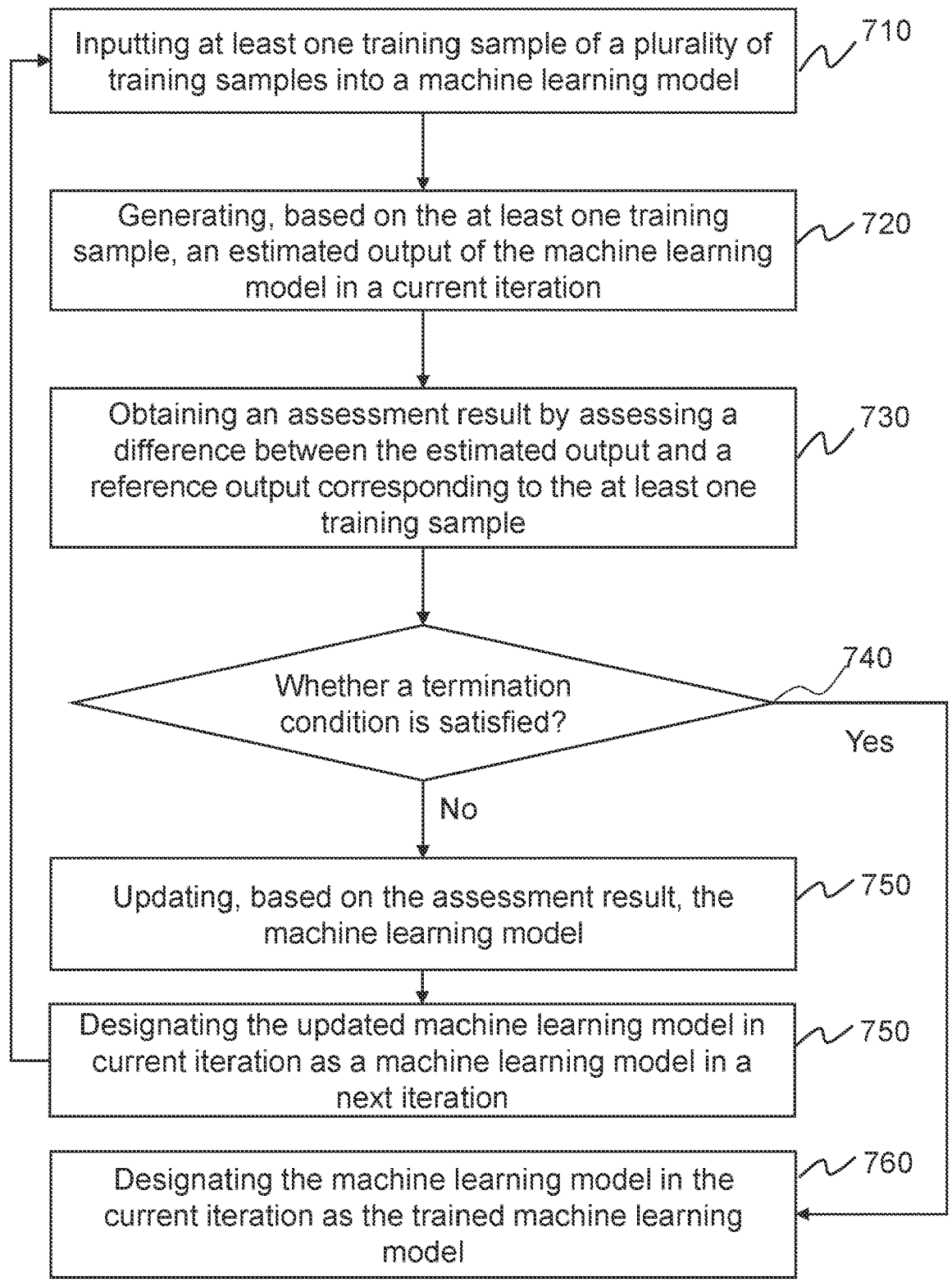
FIG. 7 is a schematic flowchart illustrating an exemplary process for training a machine learning model according to some embodiments of the present disclosure.

FIG. 7 is a schematic flowchart illustrating an exemplary process for training a machine learning model according to some embodiments of the present disclosure. In some embodiments, process 700 may be implemented as a set of instructions (e.g., an application) stored in the storage device 130, storage 220, or storage 390. The processing device 120, the processor 210 and/or the CPU 340 may execute the set of instructions, and when executing the instructions, the processing device 120, the processor 210 and/or the CPU 340 may be configured to perform the process 700. The operations of the illustrated process presented below are intended to be illustrative. In some embodiments, the process 700 may be accomplished with one or more additional operations not described and/or without one or more of the operations discussed. Additionally, the order of the operations of process 700 illustrated in FIG. 7 and described below is not intended to be limiting. In some embodiments, the training process of the trained machine learning model (as described in connection with operations 520 in FIG. 5 and/or the trained personalized machine learning model and/or the generalized machine learning model as described in FIG. 8 may be performed according to the process 700.

The trained machine learning model may be generated by training a machine learning model. In some embodiments, the machine learning model to be trained may include a convolutional neural network (CNN) model, a recurrent neural network (RNN) model, a long short term memory (LSTM) network model, a fully convolutional neural network (FCN) model, a generative adversarial network (GAN) model, a back propagation (BP) machine learning model, a radial basis function (RBF) machine learning model, a deep belief nets (DBN) machine learning model, an Elman machine learning model, or the like, or any combination thereof. The machine learning model may be composed of an input layer, at least one hidden layer, and an output layer, wherein the number of layers of the hidden layer and the number of nodes of each layer may be determined according to actual conditions and computational requirements. The machine learning model may include a plurality of parameters, such as architecture parameters, learning parameters, etc. Exemplary architecture parameters of the machine learning model may include the size of a kernel of a layer, the total count (or number) of layers, the count (or number) of nodes in each layer, a learning rate, a batch size, an epoch, etc. Exemplary learning parameters may include a connected weight between two connected nodes, a bias vector relating to a node, etc.). Before the training, the machine learning model may have one or more initial parameter values. In the training of the machine learning model, learning parameters of the machine learning model may be updated. The update of the learning parameters of the machine learning model may be also referred to as the update of the machine learning model. In some embodiments, the training process of the machine learning model may be an iterative process including one or more iterations. For illustration purposes, a current iteration of the iteration (s) is described in the following description. The current iteration may include one or more operations of the process 700.

In 710, the processing device 120 (e.g., the training sample acquisition module 450) may input at least one training sample of a plurality of training samples into the machine learning model. In some embodiments, the plurality of training samples may refer to data configured to train the machine learning model. In some embodiments, each of the plurality of training samples may include a third dose distribution with low accuracy and a fourth dose distribution with high accuracy in a specific object. The third dose distribution and the fourth dose distribution corresponding to the same object may be designated as a training sample. The third dose distribution may describe a distribution of a third count of radiation particles (also referred to as third particle count) of different positions of the specific object. The fourth dose distribution may describe a distribution of a fourth count of radiation particles (also referred to as fourth particle count) of different positions of the subject. The fourth count may exceed the third count such that the fourth dose distribution has a higher accuracy than that of the third dose distribution. In some embodiments, the fourth count may be equal to or larger than two times of the third count, so that the computational time of the third sample dose distribution can be shortened. For example, the third count of radiation particles may be $2\times10^7$, and the fourth count of radiation particles may be $8\times10^8$. The fourth dose distribution may serve as a reference output (i.e., a desired output) of the machine learning model, and the third dose distribution may serve as an input of the machine learning model.

In some embodiments, at least one of the third dose distribution or the fourth dose distribution may be determined based on personalized data of the specific object using a simulation technique (e.g., a Monte-Carlo technique). The personalized data of the specific object may include a radiotherapy treatment plan of the specific object and a density distribution of the specific object. The radiotherapy treatment plan of the subject may include a value of an energy of a particle source (i.e., a radiation source) for generating radiation, penetration depth information of radiation particles in the subject, an angle of a gantry of a radiation device, a shape of a radiation field collimated by a collimator (e.g., a multi-leaf collimator, a Y-JAW, X-JAW, etc.), a radiation dose of the radiation device, or the like, or any combination thereof. More descriptions for simulating a dose distribution may be found elsewhere in the present disclosure (e.g., FIG. 6 and the descriptions thereof).

In some embodiments, each of the plurality of training samples may include the third dose distribution of a specific object and a difference between the third dose distribution and the fourth dose distribution of the specific object. In the iterative process, the difference between the third dose distribution and the fourth dose distribution may serve as the reference output of the machine learning model in the iterative process and the third dose distribution may serve as an input of the machine learning model. In some embodiments, each of the plurality of training samples may include the third dose distribution with low accuracy and the fourth dose distribution with high accuracy in the specific object, and the personalized data of the specific object. The personalized data, the third dose distribution, and the fourth dose distribution corresponding to the same object may be designated as a training sample. In the iterative process, the fourth dose distribution may serve as a reference output (i.e., a desired output) of the machine learning model, and the third dose distribution and the personalized data may serve as an input of the machine learning model. In some embodiments, each of the plurality of training samples may include the third dose distribution with low accuracy and the personalized data of the specific object. The personalized data and the third dose distribution may be designated as a training sample. In the iterative process, the third dose distribution may serve as a reference output (i.e., a desired output) of the machine learning model, and the personalized data may serve as an input of the machine learning model.

In 720, the processing device 120 (e.g., the model training module 460) may generate an estimated output using the machine learning model based on each of the at least one training sample. The machine learning model in the current iteration may input the at least one of the plurality of training samples (e.g., the personalized data, the third dose distribution, and the fourth dose distribution) into the machine learning model. The machine learning model may generate one or more estimated outputs by processing the inputted at least one training sample. In some embodiments, if the desired output of the machine learning model is the fourth dose distribution, an estimated output may be an estimated fourth dose distribution. In some embodiments, if the desired output of the trained machine learning model is the deviation between the third dose distribution and the fourth dose distribution, an estimated output may be an estimated deviation (i.e., dose distribution error) between the third dose distribution and the fourth dose distribution.

In 730, the processing device 120 (e.g., the model training module 460) may obtain an assessment result by assessing a difference between the estimated output and a reference output corresponding to the at least one training sample. In some embodiments, to obtain the assessment result, a cost function relating to the difference between the estimated output and the reference output (e.g., the fourth dose distribution) may be used. As used herein, the cost function (or loss function) may refer to a function that measures a difference between the estimated output and the reference output (i.e., the desired output) of the machine learning model, wherein the difference may indicate the accuracy of the machine learning model. The cost function may include a log loss function, a cross-entropy loss function, a least-squares function, an index loss function, etc. In some embodiments, the assessment result may include a total error between one or more estimated outputs and one or more reference outputs corresponding to the at least one training sample inputted into the machine learning model in the same batch. In some embodiments, the assessment result may include a local error between the estimated output and the reference output corresponding to each of the at least one training sample inputted into the machine learning model in the same batch. In some embodiments, operation 730 may further include determining whether the assessment result (e.g., the local error, the total error) satisfies a condition (e.g., a threshold). In response to a determination that the assessment result does not satisfy the condition, the processing device 120 may update the learning parameters of the machine learning model until each local error satisfies the condition and/or the total error satisfies the condition.

In 740, the processing device 120 (e.g., the model training module 460) may determine whether a termination condition satisfies a criterion. The termination condition may provide an indication of whether the machine learning model is sufficiently trained. The termination condition may relate to the assessment result (e.g., a cost function) or an iteration count of the training process. For example, the processing device 120 may determine a cost function of the machine learning model and determine a value of the cost function based on the difference between the estimated output and the reference output. Further, the processing device 120 may determine the termination condition is satisfied if the value of the cost function is less than a threshold. The threshold may be default settings of the radiotherapy system 100 or may be adjustable under different situations. As another example, the termination condition may be satisfied if the value of the cost function converges. The convergence may be deemed to have occurred if the variation of the values of the cost function in two or more consecutive iterations is smaller than a threshold (e.g., a constant). As still another example, the processing device 120 may determine the termination condition is satisfied if a specified number (or count) of iterations are performed in the training process.

In response to a determination that the termination condition satisfies the criterion, the processing device 120 may proceed to operation 770. In 770, the processing device 120 may designate the machine learning model in the current iteration as the trained machine learning model (e.g., the trained machine learning model). On the other hand, in response to a determination that the termination condition is not satisfied, the processing device 120 may proceed to operation 750. In 750, the processing device 120 may update the machine learning model based on the assessment result. For example, the processing device 120 may update the value(s) of the learning parameter(s) of the machine learning model based on the value of the assessment result according to, for example, a backpropagation algorithm.

In 760, the processing device 120 (e.g., the model training module 460, the processing circuits of the processor 210) may designate the updated machine learning model in the current iteration as a machine learning model in a next iteration.

After 760, the processing device 120 may proceed to operation 710 to perform the next iteration until the termination condition is satisfied. In the next iteration, the processing device 120 may obtain multiple groups of training samples in another batch. The size of the batch may refer to a group count or number of the multiple groups of training samples. After the termination condition is satisfied in a certain iteration, the machine learning model in the certain iteration having the updated value(s) of the learning parameter(s) may be designated as the trained machine learning model.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, one or more other optional operations (e.g., a storing operation) may be added elsewhere in the process 700. In the storing operation, the processing device 120 may store information and/or data (e.g., a second training sample, the trained second machine learning model, etc.) associated with the radiotherapy system 100 in a storage device (e.g., the storage device 130) disclosed elsewhere in the present disclosure.

Figure 8:
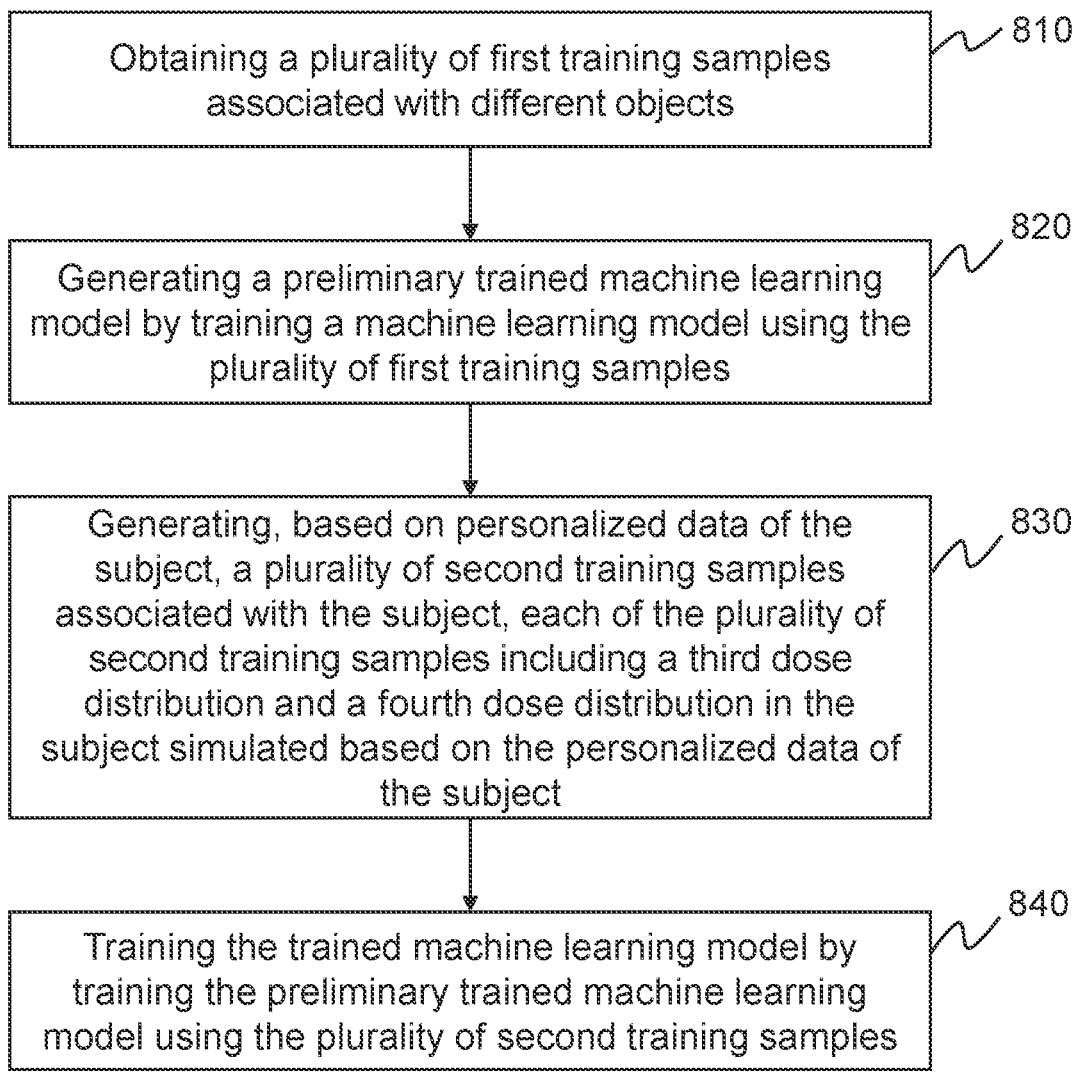
FIG. 8 is a schematic flowchart illustrating an exemplary training process of a personalized machine learning model according to some embodiments of the present disclosure.

FIG. 8 a schematic flowchart illustrating an exemplary training process of a personalized machine learning model according to some embodiments of the present disclosure. In some embodiments, process 800 may be implemented as a set of instructions (e.g., an application) stored in the storage device 130, storage 220, or storage 390. The processing device 120, the processor 210 and/or the CPU 340 may execute the set of instructions, and when executing the instructions, the processing device 120, the processor 210 and/or the CPU 340 may be configured to perform the process 800. The operations of the illustrated process presented below are intended to be illustrative. In some embodiments, the process 800 may be accomplished with one or more additional operations not described and/or without one or more of the operations discussed. Additionally, the order of the operations of process 800 illustrated in FIG. 8 and described below is not intended to be limiting.

In 810, the processing device 120 (e.g., the training sample acquisition module 450) may obtain a plurality of first training samples associated with different objects. In some embodiments, each of the plurality of first training samples may include a third dose distribution with low accuracy and a fourth dose distribution with high accuracy of one of the different objects. In some embodiments, each of the plurality of first training samples may include a third dose distribution with low accuracy and a deviation between the third dose distribution and a fourth dose distribution with high accuracy of one of the different objects. The third dose distribution may describe a distribution of a third count of radiation particles (also referred to as third particle count) of different positions of the specific object. The fourth dose distribution may describe a distribution of a fourth count of radiation particles (also referred to as fourth particle count) of different positions of the subject. The fourth count may exceed the third count such that the fourth dose distribution has a higher accuracy than that of the third dose distribution. Each of the different objects may include personalized data. The personalized data of an object may include a radiotherapy treatment plan of the object and a density distribution in the object. Different objects may correspond to different radiotherapy treatment plans and/or density distributions. The third dose distribution and/or the fourth dose distribution of an object may be determined based on the personalized data of the object using the same or different simulation techniques according to process 600 as described in FIG. 6. More descriptions of the first training samples may be found in FIGS. 6-7 and the descriptions thereof.

In 820, the processing device 120 (e.g., the model training module 460) may generate a preliminary trained machine learning model by training a machine learning model using the plurality of first training samples. The preliminary trained machine learning model may be also referred to as a generalized trained machine learning model. In some embodiments, the machine learning model may be an artificially intelligent model. In some embodiments, the machine learning model may be an unsupervised learning model. In some embodiments, the machine learning model may be a supervised learning model. The preliminary trained machine learning model may be obtained using the plurality of first training samples by the processing device 120 according to process 700. In some embodiments, in the training process, the fourth dose distribution may serve as a reference output of the machine learning model and the third dose distribution and information of at least one object may serve as an input of the machine learning model In 830, the processing device 120 (e.g., the training sample acquisition module 450) may obtain a plurality of second training samples associated with a subject. In some embodiments, the subject (e.g., the subject as described in FIG. 5) may be one of the different objects as described in operation 810. In some embodiments, the subject may be different from each of the different objects as described in operation 810. Each of the plurality of second training samples may be generated based on personalized data of the subject. In some embodiments, each of the plurality of second training samples including a third dose distribution and a fourth dose distribution in the subject simulated based on the personalized data of a specific object. The third dose distribution may describe a distribution of a third count of radiation particles (also referred to as third particle count) of the specific object. The fourth dose distribution may describe a distribution of a fourth count of radiation particles (also referred to as fourth particle count) of the same object. The fourth count may exceed the third count such that the fourth dose distribution has a higher accuracy than that of the third dose distribution. Each of the specific objects may include personalized data. In some embodiments, the personalized data of the specific object may include a radiotherapy treatment plan of the specific object and a density distribution in the specific object. More descriptions of the second training samples may be found in FIG. 6 and the descriptions thereof.

In 840, the processing device 120 (e.g., the model training module 460) may obtain a target trained machine learning model by training the preliminary trained machine learning model using the plurality of second training samples. The target trained machine learning model may be also referred to as a personalized trained machine learning model. In some embodiments, the target machine learning model may be trained using the plurality of second training samples according to process 700 as described in FIG. 7.

As the third dose distribution and the fourth dose distribution of each of the plurality of second training samples are determined based on the personalized data of the subject, a dose distribution of the subject determined using the personalized trained machine learning model may be more accuracy that a dose distribution of the subject determined based on the generalized trained machine learning model.

In some embodiments, after obtaining a trained machine learning model (e.g., the generalized trained machine learning model and/or the personalized trained machine learning model), the processing device 120 (e.g., the storage module 470) may store the trained machine learning model in one or more storage devices (e.g., the storage device 130, the storage 220, and/or the storage 390) of the radiotherapy system 100 and/or an external data source. Therefore, a processing device same as or different from the processing device 120 may obtain the trained machine learning model from the storage device(s) or the external data source when applying the trained machine learning model to determine a dose distribution of the subject or other objects.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, one or more other optional operations (e.g., a storing operation) may be added elsewhere in the process 800. In the storing operation, the processing device 120 may store information and/or data (e.g., a second training sample, the trained second machine learning model, etc.) associated with the radiotherapy system 100 in a storage device (e.g., the storage device 130) disclosed elsewhere in the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer-readable media having computer-readable program code embodied thereon.

A non-transitory computer-readable signal medium may include a propagated data signal with computer readable program code embodied therein, for example, in baseband or as part of a carrier wave. Such a propagated signal may take any of a variety of forms, including electromagnetic, optical, or the like, or any suitable combination thereof. A computer-readable signal medium may be any computer-readable medium that is not a computer-readable storage medium and that may communicate, propagate, or transport a program for use by or in connection with an instruction execution system, apparatus, or device. Program code embodied on a computer-readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C#, VB. NET, Python or the like, conventional procedural programming languages, such as the "C" programming language, Visual Basic, Fortran, Perl, COBOL, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, e.g., an installation on an existing server or mobile device.

Similarly, it should be appreciated that in the foregoing description of embodiments of the present disclosure, various features are sometimes grouped together in a single embodiment, figure, or description thereof to streamline the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate" or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system, comprising:
    at least one storage device storing a set of instructions; and
    at least one processor in communication with the at least one storage device, when executing the stored set of instructions, the at least one processor causes the system to perform operations including:
        obtaining personalized data of a subject, the personalized data of the subject including a radiotherapy treatment plan of the subject and a density distribution in the subject, the density distribution in the subject being configured to be used to characterize densities of different portions of the subject;
        generating, based on the radiotherapy treatment plan of the subject, a first equivalent count of simulation radiation particles, the simulation radiation particles being configured to be used to simulate a first dose distribution corresponding to the radiotherapy treatment plan of the subject;
        simulating, based on the density distribution in the subject, transport of each of the simulation radiation particles; and
        determining, based on the transport of each of the at least a portion of the radiation particles, the first dose distribution in at least a portion of the subject.

2. The system of claim 1, wherein to simulate, based on the density distribution in the subject, transport of each of the simulation radiation particles, the at least one processor causes the system to perform the operations including:
    determining, based on the density distribution in the subject, the transport of each of the simulation radiation particles using a Monte Carlo algorithm.

3. The system of claim 1, wherein the density distribution in the subject is obtained based on image data of the subject.

4. The system of claim 1, wherein the radiotherapy treatment plan of the subject includes at least one of a value of an energy of a particle source, a penetration depth of radiation particles in the subject, an angle of a gantry of a radiation device, a shape of a radiation field collimated by a collimator, a radiation dose of the radiation device.

5. The system of claim 1, wherein to simulate, based on the density distribution in the subject, transport of each of the simulation radiation particles, the at least one processor causes the system to perform the operations including:
    obtaining a particle transport model; and
    simulating, based on the density distribution in the subject, the transport of each of the simulation radiation particles in the particle transport model.

6. The system of claim 1, wherein the at least one processor causes the system to perform the operations including:
    generating, based on the first dose distribution, a second dose distribution corresponding to a second equivalent count of simulation radiation particles in the at least a portion of the subject, the second equivalent count exceeding the first equivalent count.

7. The system of claim 6, wherein to generate, based on the first dose distribution, a second dose distribution corresponding to a second equivalent count of simulation radiation particles in the at least a portion of the subject, the at least one processor causes the system to perform the operations including:
    obtaining a trained machine learning model; and
    generating, based on the first dose distribution and the trained machine learning model, the second dose distribution corresponding to the second equivalent count of simulation radiation particles in the at least a portion of the subject.

8. The system of claim 7, wherein the trained machine learning model is obtained according to a process including:
    obtaining a plurality of training samples; and
    generating the trained machine learning model by iteratively updating, based on the plurality of training samples, parameter values of a machine learning model in an iterative process, for each iteration of the iterative process,
        inputting at least one training sample of the plurality of training samples into the machine learning model;
        generating, based on the at least one training sample, an estimated output using the machine learning model;
        obtaining an assessment result by assessing a difference between the estimated output and a reference output corresponding to the at least one training sample;
        determining whether a termination condition is satisfied;
        based on a determination whether the termination condition is satisfied,
            updating, based on the assessment result, at least some of the parameter values of the machine learning model in response to the determination that the termination condition is not satisfied; or
            designating the machine learning model with the parameter values updated in a last iteration as the trained machine learning model in response to the determination that the termination condition is satisfied.

9. The system of claim 8, wherein each of the plurality of training samples includes a third dose distribution and a fourth dose distribution of a specific object, the fourth dose distribution serves as the reference output of the machine learning model in the iterative process, and the third dose distribution serves as an input of the machine learning model in the iterative process, the third dose distribution describing a distribution of a count of radiation particles, the fourth dose distribution describing a distribution of a count of radiation particles exceeding the count of the radiation particles corresponding to the third dose distribution.

10. The system of claim 9, wherein the count of the radiation particles corresponding to the fourth dose distribution equal to two times of the count of the radiation particles corresponding to the third dose distribution.

11. The system of claim 9, wherein at least one of the third dose distribution or the fourth dose distribution is determined based on personalized data of the specific object using a simulation technique, the personalized data of the specific object including a radiotherapy treatment plan of the specific object and a density distribution in the specific object.

12. The system of claim 8, wherein each of the plurality of training samples includes a third dose distribution of a specific object and a deviation between the third dose distribution and a fourth dose distribution of the specific object, the deviation between the third dose distribution and the fourth dose distribution serves as the reference output of the machine learning model in the iterative process, the third dose distribution serves as an input of the machine learning model in the iterative process, the third dose distribution describing a distribution of a count of radiation particles, the fourth dose distribution describing a distribution of a count of radiation particles exceeding the count of the radiation particles corresponding to the third dose distribution.

13. The system of claim 7, wherein to generate, based on the first dose distribution and the trained machine learning model, the second dose distribution in the at least a portion of the subject, the at least one processor causes the system to perform the operations including:
inputting the first dose distribution into the trained machine learning model; and
designating an output of the trained machine learning model as the second dose distribution.

14. The system of claim 7, wherein to generate, based on the first dose distribution and the trained machine learning model, the second dose distribution in the at least a portion of the subject, the at least one processor causes the system to perform the operations including:
inputting the first dose distribution into the trained machine learning model;
generating a deviation between the first dose distribution and the second dose distribution using the trained machine learning model by processing the first dose distribution; and
determining, based on the first dose distribution and the deviation between the first dose distribution and the second dose distribution, the second dose distribution.

15. The system of claim 7, wherein to generate, based on the first dose distribution and the trained machine learning model, the second dose distribution in the at least a portion of the subject, the at least one processor causes the system to perform the operations including:
inputting the first dose distribution and the personalized data of the subject into the trained machine learning model; and
determining, based on an output of the trained machine learning model, the second dose distribution.

16. The system of claim 7, wherein the trained machine learning model is obtained according to a process including:
obtaining a plurality of first training samples associated with different objects;
generating a preliminary trained machine learning model by training a machine learning model using the plurality of first training samples;
generating, based on the personalized data of the subject, a plurality of second training samples associated with the subject, each of the plurality of second training samples including a third dose distribution and a fourth dose distribution in the subject simulated based on the personalized data of the subject; and
training the trained machine learning model by training the preliminary trained machine learning model using the plurality of second training samples.

17. A system, comprising:
at least one storage device storing a set of instructions; and
at least one processor in communication with the at least one storage device, when executing the stored set of instructions, the at least one processor causes the system to perform operations including:
obtaining personalized data of a subject, the personalized data of the subject including a radiotherapy treatment plan of the subject and a density distribution in the subject, the density distribution in the subject being configured to be used to characterize densities of different portions of the subject;
determining a first dose distribution corresponding to a first equivalent count of simulation radiation particles in at least a portion of the subject, the simulation radiation particles being configured to be used to simulate the first dose distribution corresponding to the radiotherapy treatment plan of the subject; and
generating, based on the first dose distribution and the personalized data of a subject, a second dose distribution corresponding to a second equivalent count of simulation radiation particles in the at least a portion of the subject.

18. The system of claim 17, wherein to generate, based on the first dose distribution and the personalized data of a subject, a second dose distribution corresponding to a second equivalent count of simulation radiation particles in the at least a portion of the subject, the at least one processor causes the system to perform the operations including:
obtaining a trained machine learning model; and
generating, based on the first dose distribution and the trained machine learning model, the second dose distribution corresponding to the second equivalent count of simulation radiation particles in the at least a portion of the subject.

19. The system of claim 18, wherein the trained machine learning model is obtained according to a process including:
obtaining a plurality of training samples; and
generating the trained machine learning model by iteratively updating, based on the plurality of training samples, parameter values of a machine learning model in an iterative process, for each iteration of the iterative process,
inputting at least one training sample of the plurality of training samples into the machine learning model;
generating, based on the at least one training sample, an estimated output using the machine learning model;
obtaining an assessment result by assessing a difference between the estimated output and a reference output corresponding to the at least one training sample;
determining whether a termination condition is satisfied;
based on a determination whether the termination condition is satisfied, updating, based on the assessment result, at least some of the parameter values of the machine learning model in response to the determination that the termination condition is not satisfied; or designating the machine learning model with the parameter values updated in a last iteration as the trained machine learning model in response to the determination that the termination condition is satisfied.

20. The system of claim 19, wherein each of the plurality of training samples includes a third dose distribution and a fourth dose distribution of a specific object, the fourth dose distribution serves as the reference output of the machine learning model in the iterative process, and the third dose distribution serves as an input of the machine learning model in the iterative process, the third dose distribution describing a distribution of a count of radiation particles, the fourth dose distribution describing a distribution of a count of radiation particles exceeding the count of the radiation particles corresponding to the third dose distribution.

* * * * *